United States Patent [19]
Chenard et al.

[11] Patent Number: 6,136,812
[45] Date of Patent: Oct. 24, 2000

[54] METHODS OF ADMINISTERING AMPA RECEPTOR ANTAGONISTS TO TREAT DYSKINESIAS ASSOCIATED WITH DOPAMINE AGONIST THERAPY

[75] Inventors: Bertrand L. Chenard, Waterford; Willard M. Welch; Frank S. Menniti, both of Mystic, all of Conn.

[73] Assignee: Pfizer Inc, New York, N.Y.

[21] Appl. No.: 09/148,974

[22] Filed: Sep. 4, 1998

Related U.S. Application Data

[60] Provisional application No. 60/058,098, Sep. 5, 1997.

[51] Int. Cl.$^7$ .................................................. A61K 31/505
[52] U.S. Cl. ............................................. 514/259
[58] Field of Search ............................................. 514/259

[56] References Cited

U.S. PATENT DOCUMENTS

| | | |
|---|---|---|
| 5,252,584 | 10/1993 | Carling et al. . |
| 5,268,378 | 12/1993 | Baker et al. . |
| 5,342,946 | 8/1994 | Hamilton et al. . |
| 5,356,902 | 10/1994 | Ornstein . |
| 5,364,876 | 11/1994 | Hamilton . |
| 5,376,748 | 12/1994 | Carling et al. . |
| 5,395,827 | 3/1995 | Rzeszotarski et al. . |
| 5,399,696 | 3/1995 | Arnold et al. . |
| 5,407,935 | 4/1995 | Bigge et al. . |
| 5,420,155 | 5/1995 | Kulagowski . |
| 5,426,106 | 6/1995 | Kulagowski . |
| 5,446,051 | 8/1995 | Ornstein . |
| 5,475,008 | 12/1995 | Carling et al. . |
| 5,504,085 | 4/1996 | Jacobsen et al. . |
| 5,510,338 | 4/1996 | Hamilton . |
| 5,514,680 | 5/1996 | Weber et al. . |
| 5,519,019 | 5/1996 | Andrasi et al. . |
| 5,521,174 | 5/1996 | Andrasi et al. . |
| 5,527,810 | 6/1996 | Ornstein . |
| 5,532,236 | 7/1996 | Jacobsen et al. . |
| 5,559,106 | 9/1996 | Jacobsen et al. . |
| 5,559,125 | 9/1996 | Kulagowski et al. . |
| 5,580,877 | 12/1996 | MacLeod . |
| 5,606,062 | 2/1997 | Huff . |
| 5,614,508 | 3/1997 | Nikam . |
| 5,614,532 | 3/1997 | Carling et al. . |
| 5,620,979 | 4/1997 | Weber et al. . |
| 5,622,952 | 4/1997 | Weber et al. . |
| 5,631,373 | 5/1997 | Cai et al. . |
| 5,639,751 | 6/1997 | Andrasi et al. . |
| 5,654,303 | 8/1997 | Kornberg et al. . |

FOREIGN PATENT DOCUMENTS

WO9743276  11/1997  WIPO .

OTHER PUBLICATIONS

Albin R.L., Greenamyre J.T. (1992) Alternative Excitotoxic Hypothesis, *Neurology*, 42, pp. 733–737.

Greenamyre J.T., et al.(1994) Antiparkinsonian Effects of Remacemide Hydrochloride, A Glutamate Antagonist, in Rodent and Primate Models of Parkinson's Disease, *Annals of Neurology*, 35, pp 655–661.

Greenamyre J.T. (1996) Pharmacological Pallidotomy With Glutamate Antagonists, *Annals of Neurolgy*, 39(5): pp. 557–558.

Klockgether T., et al. (1991) The AMPA Receptor Antagonist NBQX Has Antiparkinsonian Effects in Monoamine–depleted Rats and MPTP–Treated Monkeys, *Annals of Neurology*, 30, pp. 717–723.

Papa S.M. and Chase T.N. (1996) Levodopa–Induced Dyskinesias Improved by a Glutamate Antagonist in Parkinsonian Monkeys, *Annals of Neurology*, 39(5): pp. 574–578.

Srivastava et al, Chemical Abstracts, vol. 107, abstract No. 175980, 1986.

*Primary Examiner*—William R. A. Jarvis
*Attorney, Agent, or Firm*—Peter C. Richardson; Paul H. Ginsberg; Kristina L. Konstas

[57] ABSTRACT

The invention relates to a method of treating dyskinesias associated with dopamine agonist therapy in a mammal which comprises administering to said mammal a compound, as defined herein, which is an antagonist of the AMPA receptor. Dopamine agonist therapy, as referred to in the present invention, is generally used in the treatment of a central nervous system disorder such as Parkinson's disease.

10 Claims, No Drawings

METHODS OF ADMINISTERING AMPA RECEPTOR ANTAGONISTS TO TREAT DYSKINESIAS ASSOCIATED WITH DOPAMINE AGONIST THERAPY

This Application claims the benefit of U.S. Provisional Application No. 60/058,098, filed Sep. 5, 1997.

BACKGROUND OF THE INVENTION

This invention relates to a method of administering AMPA receptor antagonists to treat dyskinesias in mammals, such as humans, resulting from the use of dopamine agonist therapy. Dopamine agonist therapy, as referred to in the present invention, is generally used in the treatment of a central nervous system disorder such as Parkinson's disease. In particular, this invention relates to the treatment of such dyskinesias using one or more AMPA receptor antagonists that are disclosed and claimed in PCT international application number PCT/IB97/00134 (filed Feb. 17, 1997), United States provisional patent application number 60/038905 (filed Feb. 28, 1997), United States provisional patent application number 60/049082 (filed Jun. 9, 1997), United States provisional patent application number 60/049083 (filed Jun. 9, 1997), United States provisional patent application number 60/038540 (filed Feb. 28, 1997), United States provisional patent application entitled "Quinazolin-4-one AMPA Antagonists" filed Jul. 21, 1997 with Bertrand L. Chenard, Willard M. Welch, and Anthony R. Reinhold named as inventors, and United States provisional patent application entitled "Novel Atropisomers Of 2,3-Disubstituted-(5,6)-Heteroarylfused-Pyrimidin-4-ones" filed Aug. 27, 1997 with Bertrand L. Chenard and Willard M. Welch named as inventors. The foregoing United States provisional and PCT international patent applications are incorporated herein by reference in their entirety.

Dyskinesias are involuntary physical movements which may include chorea, tremor, ballism, dystonia, athetosis, myoclonus and tic. Dyskinesias often result from treatment of the physical symptoms of Parkinson's disease. Parkinson's disease is characterized by tremor, rigidity, bradykinesia and postural instability. Such motor abnormalities may be reduced by therapies which increase dopamine receptor stimulation. These therapies include drugs which directly stimulate dopamine receptors (such as bromocriptine) or increase the levels of dopamine (such as L-dopa or drugs which inhibit dopamine metabolism). In the present invention, such therapies which increase dopamine receptor stimulation are referred to generally as dopamine agonist therapy. After a period of chronic administration of dopamine agonist therapy to treat Parkinson's disease, new motor abnormalities may emerge. The motor abnormalities associated with dopamine agonist therapy include choreatic dyskinesias and dystonias. The present invention relates to the treatment of dyskinesias associated with dopamine agonist therapy in the treatment of a central nervous system (CNS) disorder, in particular Parkinson's disease, through the administration of an AMPA receptor antagonist as provided below.

The compounds that may be used in accord with the present invention are antagonists of the AMPA subtype of the glutamate receptor. Glutamate is the principal excitatory neurotransmitter in the central nervous system of mammals. Glutamate synaptic transmission is mediated by several families of receptors including the α-amino-3-hydroxy-5-methyl-4-isoxazolepropionic acid (AMPA), N-methyl-D-aspartate (NMDA), kainic acid (KA), and metabotropic receptors. The AMPA receptor subtype mediates fast excitatory transmission throughout the brain, including areas involved in movement. By inhibiting the AMPA receptor through administration of an AMPA receptor antagonist, dyskinesias associated with dopamine agonist therapy may be treated in accord with the present invention as described below.

AMPA receptor antagonists are referred to in several published patents including the following issued patents (listed by patent number followed by issue date in parentheses): U.S. Pat. Nos. 5,654,303 (Aug. 5, 1997); 5,639,751 (Jun. 17, 1997); 5,614,532 (Mar. 25, 1997); 5,614,508 (Mar. 25, 1997); 5,606,062 (Feb. 25, 1997); 5,580,877 (Dec. 3, 1996); 5,559,125 (Sep. 24, 1996); 5,559,106 (Sep. 24, 1996); 5,532,236 (Jul. 2, 1996); 5,527,810 (Jun. 18, 1996); 5,521,174 (May 28, 1996); 5,519,019 (May 21, 1996); 5,514,680 (May 7, 1996); 5,631,373 (May 20, 1997); 5,622,952 (Apr. 22, 1997); 5,620,979 (Apr. 15, 1997); 5,510,338 (Apr. 23, 1996); 5,504,085 (Apr. 2, 1996); 5,475,008 (Dec. 12, 1995); 5,446,051 (Aug. 29, 1995); 5,426,106 (Jun. 20, 1995); 5,420,155 (May 30, 1995); 5,407,935 (Apr. 18, 1995); 5,399,696 (Mar. 21, 1995); 5,395,827 (Mar. 7, 1995); 5,376,748 (Dec. 27, 1994); 5,364,876 (Nov. 15, 1994); 5,356,902 (Oct. 18, 1994); 5,342,946 (Aug. 30, 1994); 5,268,378 (Dec. 7, 1993); and 5,252,584 (Oct. 12, 1993).

SUMMARY OF THE INVENTION

This invention relates to a method of treating dyskinesias associated with dopamine agonist therapy in a mammal, such as a human, which comprises administering to said mammal an amount of a compound within group (A), (B), (C), (D), (E), or (F), or a pharmaceutically acceptable salt of said compound, that is effective in treating said dyskinesia, wherein groups (A), (B), (C), (D), (E), and (F) are defined as follows:

(A) (S)-3-(2-chloro-phenyl)-2-[2-(5-diethylaminomethyl-2-fluoro-phenyl)-vinyl]-6-fluoro-3H-quinazolin-4-one;

(S)-3-(2-chloro-phenyl)-2-[2-(6-diethylaminomethyl-pyridin-2-yl)-vinyl]-6-fluoro-3H-quinazolin-4-one;

(S)-3-(2-chloro-phenyl)-2-[2-(4-diethylaminomethyl-pyridin-2-yl)-vinyl]-6-fluoro-3H-quinazolin-4-one;

(S)-3-(2-chloro-phenyl)-2-[2-(6-ethylaminomethyl-pyridin-2-yl)-vinyl]-6-fluoro-3H-quinazolin-4-one;

(S)-3-(2-bromo-phenyl)-2-[2-(6-diethylaminomethyl-pyridin-2-yl)-vinyl]-6-fluoro-3H-quinazolin-4-one;

(S)-3-(2-chloro-phenyl)-6-fluoro-2-[2-(6-methoxymethyl-pyridin-2-yl)-vinyl]-3H-quinazolin-4-one;

(S)-3-(2-chloro-phenyl)-6-fluoro-2-[2-(4-Methyl-pyrimidine-2-yl)-vinyl]-3H-quinazolin-4-one;

(S)-3-(2-chloro-phenyl)-6-fluoro-2-{2-[6-(isopropylamino-methyl)-pyridin-2-yl]-ethyl}-3H-quinazolin-4-one;

(S)-6-fluoro-2-[2-(2-methyl-thiazol-4-yl)-vinyl]-3-(2-methyl-phenyl)-3H-quinazolin-4-one;

(S)-3-(2-chloro-phenyl)-6-fluoro-2-[2-(2-methyl-thiazol-4-yl)-vinyl]-3H-quinazolin-4-one;

(S)-2-[2-(2-dimethylaminomethyl-thiazol-4-yl)-vinyl]-6-fluoro-3-(2-fluoro-phenyl)-3H-quinazolin-4-one;

(S)-3-(2-bromo-phenyl)-6-fluoro-2-[2-(2-methyl-thiazol-4-yl)-vinyl]-3H-quinazolin-4-one;

(S)-3-(2-chloro-phenyl)-2-[2-(2-methyl-thiazol-4-yl)-vinyl]-3H-quinazolin-4-one;

(S)-3-(2-chloro-phenyl)-6-fluoro-2-(2-pyridin-2-yl-vinyl)-3H-quinazolin-4-one;

(S)-3-(2-bromo-phenyl)-2-(2-pyridin-2-yl-vinyl)-3H-quinazolin-4-one;

(S)-6-chloro-2-(2-pyridin-2-yl-vinyl)-3-o-tolyl-3H-quinazolin-4-one;

(S)-3-(2-chloro-phenyl)-2-[2-(6-methyl-pyridin-2-yl)-vinyl]-3H-quinazolin-4-one;

(S)-6-chloro-2-[2-(6-methyl-pyridin-2-yl)-vinyl]-3-o-totyl-3H-quinazolin-4-one;

(S)-3-(2-chloro-phenyl)-6-fluoro-2-(2-pyridin-2-yl-ethyl)-3H-quinazolin-4-one;

(S)-6-{2-[3-(2-chloro-phenyl)-6-fluoro-4-oxo-3,4-dihydro-quinazolin-2-yl]-vinyl}-pyridine-2-carbaldehyde;

(S)-3-(2-chloro-phenyl)-6-fluoro-2-[2-(6-methylaminomethyl-pyridin-2-yl)-vinyl]-3H-quinazolin-4-one;

(S)-N-(6-{2-[3-(2-chloro-phenyl)-6-fluoro-4-oxo-3,4-dihydro-quinazolin-2-yl]-vinyl}-pyridin-2-ylmethyl)-N-methyl-acetamide;

(S)-6-{2-[3-(2-chloro-phenyl)-6-fluoro-4-oxo-3,4-dihydro-quinazolin-2-yl]-vinyl}-pyridine-2-carbonitrile;

(S)-3-(2-fluoro-phenyl)-2-(2-pyridin-2-yl-vinyl)-3H-quinazolin-4-one;

(S)-3-(2-bromo-phenyl)-6-fluoro-2-(2-pyridin-2-yl-vinyl)-3H-quinazolin-4-one;

(S)-3-(4-bromo-2-chloro-phenyl)-6-fluoro-2-(2-pyridin-2-yl-vinyl)-3H-quinazolin-4-one;

(S)-3-(2-chloro-phenyl)-2-[2-(6-diethylaminomethyl-pyridin-2-yl)-vinyl]-3H-quinazolin-4-one;

(S)-N-(6-{2-[3-(2-chloro-phenyl)-6-fluoro-4-oxo-3,4-dihydro-quinazolin-2-yl]-vinyl}-pyridin-2-ylmethyl)-N-ethyl-acetamide;

(S)-3-(2-chloro-phenyl)-6-fluoro-2-[2-(6-fluoromethyl-pyridin-2-yl)-vinyl]-3H-quinazolin-4-one;

(S)-3-(2-chloro-phenyl)-6-fluoro-2-[2-(6-pyrrolidin-1-ylmethyl-pyridin-2-yl)-ethyl]-3H-quinazolin-4-one;

(S)-3-(2-chloro-phenyl)-2-[2-(6-{[ethyl-(2-hydroxy-ethyl)-amino]-methyl}-pyridin-2-yl)-vinyl]-6-fluoro-3H-quinazolin-4-one;

(S)-3-(2-chloro-phenyl)-6-fluoro-2-{2-[6-(isopropylamino-methyl)-pyridin-2-yl]-vinyl}-3H-quinazolin-4-one;

(S)-3-(2-chloro-phenyl)-6-fluoro-2-{2-[6-(2-methyl-piperidin-1-ylmethyl)-pyridin-2-yl]-vinyl}-3H-quinazolin-4-one;

(S)-3-(2-chloro-phenyl)-2-[2-(6-ethoxymethyl-pyridin-2-yl)-vinyl]-6-fluoro-3H-quinazolin-4-one;

(S)-3-(2-chloro-phenyl)-2-{2-[6-(2,5-dihydro-pyrrol-1-ylmethyl)-pyridin-2-yl]-vinyl}-6-fluoro-3H-quinazolin-4-one;

(S)-3-(2-chloro-phenyl)-6-fluoro-2-{2-[6-(4-methyl-piperidin-1-ylmethyl)-pyridin-2-yl]-vinyl}-3H-quinazolin-4-one;

(S)-6-bromo-2-[2-(6-methyl-pyridin-2-yl)-vinyl]-3-o-tolyl-3H-quinazolin-4-one;

(S)-6-bromo-2-(2-pyridin-2-yl-vinyl)-3-o-tolyl-3H-quinazolin-4-one;

(S)-6-fluoro-3-(2-fluoro-phenyl)-2-(2-pyridin-2-yl-vinyl)-3H-quinazolin-4-one;

(S)-3-(2-chloro-phenyl)-6-methyl-2-(2-pyridin-2-yl-vinyl)-3H-quinazolin-4-one;

(S)-3-(2-chloro-phenyl)-2-[2-(6-dimethylaminomethyl-pyridin-2-yl)-vinyl]-6-fluoro-3H-quinazolin-4-one;

(S)-6-fluoro-3-(2-fluoro-phenyl)-2-[2-(6-methyl-pyridin-2-yl)-vinyl]-3H-quinazolin-4-one;

(S)-3-(2-chloro-phenyl)-2-[2-(6-{[(2-dimethylamino-ethyl)-methyl-amino]-methyl}-pyridin-2-yl)-vinyl]-6-fluoro-3H-quinazolin-4-one;

(S)-3-(2-chloro-phenyl)-6-fluoro-2-[2-(6-hydroxymethyl-pyridin-2-yl)-vinyl]-3H-quinazolin-4-one;

(S)-acetic acid 6-{2-[3-(2-chloro-phenyl)-6-fluoro-4-oxo-3,4-dihydro-quinazolin-2-yl]-vinyl}-pyridin-2-yl methyl ester;

(S)-6-{2-[3-(2-bromo-phenyl)-6-fluoro-4-oxo-3,4-dihydro-quinazolin-2-yl]-vinyl}-pyridine-2-carbaldehyde;

(S)-3-(2-bromo-phenyl)-2-[2-(6-diethylaminomethyl-pyridin-2-yl)-vinyl]-3H-quinazolin-4-one;

(S)-acetic acid 6-{2-[3-(2-bromo-phenyl)-6-fluoro-4-oxo-3,4-dihydro-quin-azolin-2-yl]-vinyl}-pyridin-2-ylmethyl ester;

(S)-diethylamino-acetic acid 6-{2-[3-(2-chloro-phenyl)-6-fluoro-4-oxo-3,4-dihydro-quinazolin-2-yl]-vinyl}-pyridin-2-ylmethyl ester;

(S)-3-(2-chloro-phenyl)-2-[2-(6-difluoromethyl-pyridin-2-yl)-vinyl]-6-fluoro-3H-quinazolin-4-one;

(S)-3-(2-chloro-phenyl)-6-fluoro-2-[2-(6-methoxy-pyridin-2-yl)-vinyl]-3H-quinazolin-4-one;

(S)-2-{2[3-(2-chloro-phenyl)-6-fluoro-4-oxo-3,4-dihydro-quinazolin-2-yl]-vinyl}-6-methyl-nicotinonitrile;

(S)-2-{2-[3-(2-chloro-phenyl)-6-fluoro-4-oxo-3,4-dihydro-quinazolin-2-yl]-ethyl}-6-methyl-nicotinonitrile;

(S)-3-(2-chloro-phenyl)-6-fluoro-2-(2-pyrimidine-2-yl-ethyl)-3H-quinazolin-4-one;

(S)-3-(2-chloro-phenyl)-2-[2-(4,6-dimethyl-pyrimidine-2-yl)-vinyl]-6-fluoro-3H-quinazolin-4-one;

(S)-2-{2[3-(2-chloro-phenyl)-6-fluoro-4-oxo-3,4-dihydro-quinazolin-2-yl]-vinyl}-nicotinonitrile;

(S)-3-(2-chloro-phenyl)-6-fluoro-2-(2-{6-[(3-methyl-butylamino)-methyl]-pyridin-2-yl}-ethyl)-3H-quinazolin-4-one;

(S)-2-{2-[3-(2-chloro-phenyl)-6-fluoro-4-oxo-3,4-dihydro-quinazolin-2-yl]-ethyl}-nicotinonitrile;

(S)-2-[2-(6-chloro-4-oxo-3-o-totyl-3,4-dihydro-quinazolin-2-yl)-vinyl]-benzonitrile;

(S)-2-{2[3-(2-chloro-phenyl)-6-fluoro-4-oxo-3,4-dihydro-quinazolin-2-yl]-vinyl}-4-methyl-benzonitrile;

(S)-3-(2-chloro-phenyl)-6-fluoro-2-[2-(6-hydroxymethyl-pyridin-2-yl)-vinyl]-3H-quinazolin-4-one; and (S)-3-(2-chloro-phenyl)-6-fluoro-2-[2-(6-pyrrolidin-1-ylmethyl-pyridin-2-yl)-vinyl]-3H-quinazolin-4-one;

(B) (S)-6-fluoro-2-[2-(2-fluoro-phenyl)-vinyl]-3-(2-methyl-pyridin-3-yl)-3H-quinazolin-4-one;

(S)-2-{2-[6-fluoro-3-(2-methyl-pyridin-3-yl)-4-oxo-3,4-dihydro-quinazolin-2-yl]-vinyl}-benzonitrile;

(S)-2-{2-[6-fluoro-3-(2-methylpyridin-3-yl)-4-oxo-3,4-dihydroquinazolin-2-yl]-vinyl}-benzonitrile;

(S)-2-{2-[3-(2-chloro-pyridin-3-yl)-6-fluoro-4-oxo-3,4-dihydroquinazolin-2-yl]-vinyl}-benzonitrile;

(S)-2-{2-[6-fluoro-3-(2-methyl-pyridin-3-yl)-4-oxo-3,4-dihydro-quinazolin-2-yl]-vinyl}-4-methyl-benzonitrile;

(S)-2-{2-[3-methyl-pyridin-3-yl)-4-oxo-3,4-dihydro-quinazolin-2-yl]-vinyl}-benzonitrile;

(S)-6-fluoro-3-(2-methyl-pyridin-3-yl)-2[2-(thiazol-2-yl)-vinyl]-3H-quinazolin-4-one;

(S)-6-fluoro-3-(2-methyl-pyridin-3-yl)-2-[2-(2-methyl-thiazol-4-yl)-vinyl]-3H-quinazolin-4-one;

(S)-6-fluoro-3-(2-methyl-pyridin-3-yl)-2-[2-(4-methyl-thiazol-2-yl)-vinyl]-3H-quinazolin-4-one;

(S)-2-[2-(5-diethylaminomethyl-2-fluoro-phenyl)-vinyl]-6-fluoro-3-(2-methyl-pyridin-3-yl)-3H-quinazolin-4-one;

(S)-6-fluoro-2-[2-(2-fluoro-5-pyrrolidin-1-ylmethyl-phenyl)-vinyl]-3-(2-methyl-pyridin-3-yl)-3H-quinazolin-4-one;

(S)-3-(2-chloro-pyridin-3-yl)-2-[2-(2-fluoro-phenyl)-vinyl]-3-H-quinazolin-4-one;

(S)-3-(2-chloro-pyridin-3-yl)-6-fluoro-2-[2-(6-methyl-phenyl-2-yl)-vinyl]-3H-quinazolin-4-one;

(S)-3-(2-chloro-pyridin-3-yl)-6-fluoro-2-[2-(fluoro-phenyl)-vinyl]-3H-quinazolin-4-one;

(S)-6-chloro-2-[2-(2-fluoro-phenyl)-vinyl]-3-(2-methyl-pyridin-3-yl)-3H-quinazolin-4-one;

(S)-6-chloro-2-[2-(2-fluoro-phenyl)-vinyl]-3-(3-methyl-1-oxy-pyridin-4-yl)-3H-quinazolin-4-one;

(S)-3-{2-(3-(2-chloro-pyridin-3-yl)-6-fluoro-4-oxo-3,4-dihydro-quinazolin-2-yl]-vinyl}-benzaldehyde;

(S)-3-{2-[3-(2-chloro-pyridin-3-yl)-4-oxo-3,4-dihydro-quinazolin-2-yl]-vinyl}-benzaldehyde;

(S)-3-(2-chloro-pyridin-3-yl)-6-fluoro-2-[2-(3-hydroxymethyl-phenyl)-vinyl]-3H-quinazolin-4-one;

(S)-3-(2-chloro-pyridin-3-yl)-2-{2-[3(1,4-dioxa-8-aza-spiro[4.5]dec-8-ylmethyl)-phenyl]-vinyl}-6-fluoro-3H-quinazolin-4-one;

(S)-3-(2-chloro-pyridin-3-yl)-6-fluoro-2-{2-[3-(4-pyrrolidin-1-yl-piperidin-1-ylmethyl)-phenyl]-vinyl}-3H-quinazolin-4-one;

(S)-2-{2-[3-(2-chloro-pyridin-3-yl)-6-fluoro-4-oxo-3,4-dihydro-quinazolin-2-yl]-vinyl}-benzonitrile;

(S)-2-{2-[3-(2-chloro-pyridin-3-yl)-4-oxo-3,4-dihydro-quinazolin-2-yl]-vinyl}-benzonitrile;

(S)-2-[2-(2-fluoro-phenyl)-vinyl]-3-2-methyl-pyridin-3-yl)-3H-quinazolin-4-one;

(S)-3-(2-chloro-pyridin-3-yl)-6-fluoro-2-[2-hydroxyphenyl)-vinyl]-3H-quinazolin-4-one;

(S)-6-fluoro-3-(2-methyl-pyridin-3-yl)-2-[2-(2-methyl-thiazol-4-yl)-ethyl]-3H-quinazolin-4-one;

(S)-6-fluoro-3-(2-chloro-pyridin-3-yl)-2-[2-(2-dimethylamino-methylthiazol-4-yl)-vinyl]-3H-quinazolin-4-one;

(S)-2-[2-(5-Diethylaminomethyl-2-fluoro-phenyl)-vinyl]-6-fluoro-3-(4-methyl-pyridin-3-yl)-3H-quinazolin-4-one;

(S)-4-Diethylaminomethyl-2-{2-[6-fluoro-3(4methyl-pyridin-3-yl)-4-oxo-3,4-dihydro-quinazolin-2-yl]-vinyl}-benzonitrile;

(S)-2-[2-(5-Diethylaminomethyl-2-fluoro-phenyl)-vinyl]-6-fluoro-3-(3-methyl-pyrazin-2-yl)-3H-quinazolin-4-one;

(S)-6-fluoro-3-(2-methyl-pyridin-3-yl)-2-[2-(2-dimethylamino-methylthiazol-4-yl)-vinyl]-3H-quinazolin-4-one;

(S)-6-fluoro-3-(2-methyl-pyridin-3-yl)-2-[2-(2-methyl-oxazol-4-yl)-vinyl]-3H-quinazolin-4-one;

(S)-6-fluoro-3-(2-chloro-pyridin-3-yl)-2-[2-(thiazol-2-yl)-vinyl]-3H-quinazolin-4-one;

(S)-6-fluoro-3-(4-methyl-pyridin-3-yl)-2-[2-(4-methyl-thiazol-2-yl)-vinyl]-3H-quinazolin-4-one;

(S)-3-(2-chloro-pyridin-3-yl)-6-fluoro-2-[2-(2-hydroxyphenyl)-vinyl]-3H-quinazolin-4-one; and, (S)-6-fluoro-2-[2-(2-fluoro-5-pyrrolidin-1-ylmethyl-phenyl)-ethyl]-3-(2-methyl-pyridin-3-yl)-3H-quinazolin-4-one;

(C)-3-(2-chloro-phenyl)-6-fluoro-2-(2-pyridin-2-yl-vinyl)-3H-quinazolin-4-one;

3-(2-bromo-phenyl)-2-(2-pyridin-2-yl-vinyl)-3H-quinazolin-4-one;

6-chloro-2-(2-pyridin-2-yl-vinyl)-3-o-tolyl-3H-quinazolin-4-one;

3-(2-chloro-phenyl)-2-[2-(6-methyl-pyridin-2-yl)-vinyl]-3H-quinazolin-4-one;

6-chloro-2-[2-(6-methyl-pyridin-2-yl)-vinyl]-3-o-tolyl-3H-quinazolin-4-one;

3-(2-chloro-phenyl)-6-fluoro-2-(2-pyridin-2-yl-ethyl)-3H-quinazolin-4-one;

6-{2-[3-(2-chloro-phenyl)-6-fluoro-4-oxo-3,4-dihydro-quinazolin-2-yl]-vinyl}-pyridine-2-carbaldehyde;

3-(2-chloro-phenyl)-6-fluoro-2-[2-(6-methylaminomethyl-pyridin-2-yl)-vinyl]-3H-quinazolin-4-one;

N-(6-{2-[3-(2-chloro-phenyl)-6-fluoro-4-oxo-3,4-dihydro-quinazolin-2-yl]-pyridin-2-ylmethyl)-N-methyl-acetamide;

3-(2-chloro-phenyl)-2-[2-(4-diethylaminomethyl-pyridin-2-yl)-vinyl]-6-fluoro-3H-quinazolin-4-one;

6-{2-[3-(2-chloro-phenyl)-6-fluoro-4-oxo-3,4-dihydro-quinazolin-2-yl]-vinyl}pyridine-2-carbonitrile;

3-(2-fluoro-phenyl)-2-(2-pyridin-2-yl-vinyl)-3H-quinazolin-4-one;

3-(2-bromo-phenyl)-6-fluoro-2-(2-pyridin-2-yl-vinyl)-3-H-quinazolin-4-one;

3-(4-bromo-2-chloro-phenyl)-6-fluoro-2-(2-pyridin-2-yl-vinyl)-3H-quinazolin-4-one;

3-(2-chloro-phenyl)-2-[2-(6-diethylaminomethyl-pyridin-2-yl)-vinyl]-3H-quinazolin-4-one;

N-(6-{2-[3-(2-chloro-phenyl)-6-fluoro-4-oxo-3,4-dihydro-quinazolin-2-yl]-vinyl}-pyridin-2-ylmethyl)-N-ethyl-acetamide;

3-(2-chloro-phenyl)-6-fluoro-2-[2-(6-fluoromethyl-pyridin-2-yl)-vinyl]-3H-quinazolin-4-one;

3-(2-chloro-phenyl)-6-fluoro-2-(6-pyrrolidin-1-ylmethyl-pyridin-2-yl)-ethyl]-3H-quinazolin-4-one;

3-(2-chloro-phenyl)-2-[2-(6-{[ethyl-(2-hydroxy-ethyl)-amino]-methyl}-pyridin-2-yl)-vinyl]-6-fluoro-3H-quinazolin-4-one;

3-(2-chloro-phenyl)-6-fluoro-2-{2-[6-(isopropylamino-methyl)-pyridin-2-yl]-vinyl}-3H-quinazolin-4-one;

3-(2-chloro-phenyl)-6-fluoro-2-{2-[6-(2-methyl-piperidin-1-ylmethyl)-pyridin-2-yl]-vinyl}-3H-quinazolin-4-one;

3-(2-chloro-phenyl)-2-[2-(6-ethylaminomethyl-pyridin-2-yl)-vinyl]-6-fluoro-3H-quinazolin-4-one;

3-(2-chloro-phenyl)-2-[2-(6-ethoxymethyl-pyridin-2-yl)-vinyl]-6-fluoro-3H-quinazolin-4-one;

3-(2-chloro-phenyl)-2-{2-[6-(2,5-dihydro-pyrrol-1-ylmethyl)-pyridin-2-yl]-vinyl}-6-fluoro-3H-quinazolin-4-one;

3-(2-chloro-phenyl)-6-fluoro-2-{2-[6-(4-methyl-piperidin-1-ylmethyl)-pyridin-2-yl]-vinyl}-3H-quinazolin-4-one;

6-bromo-2-[2-(6-methyl-pyridin-2-yl)-vinyl]-3-o-tolyl-3H-quinazolin-4-one;

6-bromo-2-(2-pyridin-2-yl-vinyl)-3-o-tolyl-3H-quinazolin-4-one;

6-fluoro-3-(2-fluoro-phenyl)-2-(2-pyridin-2-yl-vinyl)-3H-quinazolin-4-one;

1-benzyl-5-(2-methyl-[1,3dioxolan-2-yl)-2-oxo-2,3-dihydro-1H-indole-3-carboxylic acid (3-phenylcarbamoyl-phenyl)-amide;

3-(2-chloro-phenyl)-6-methyl-2-(2-pyridin-2-yl-vinyl)-3H-quinazolin-4-one;

3-(2-chloro-phenyl)-2-[2-(6-dimethylaminomethyl-pyridin-2-yl)-vinyl]-6-fluoro-3H-quinazolin-4-one;

6-fluoro-3-(2-fluoro-phenyl)-2-[2-(6-methyl-pyridin-2-yl)-vinyl]-3H-quinazolin-4-one;

3-(2-chloro-phenyl)-2-[2-(6-{[(2-dimethylamino-ethyl)-methyl-amino]-methyl}-pyridin-2-yl)-vinyl]-6-fluoro-3H-quinazolin-4-one;

3-(2-chloro-phenyl)-6-fluoro-2-[2-(6-hydroxymethyl-pyridin-2-yl)-vinyl]-3H-quinazolin-4-one;

acetic acid 6-{2-[3-(2-chloro-phenyl)-6-fluoro-4-oxo-3,4-dihydro-quinazolin-2-yl]-vinyl}-pyridin-2-ylmethyl ester;

6-{2-[3-(2-bromo-phenyl)-6-fluoro-4-oxo-3,4-dihydro-quinazolin-2-yl]-vinyl}-pyridine-2-carbaldehyde;

3-(2-bromo-phenyl)-2-[2-(6-diethylaminomethyl-pyridin-2-yl)-vinyl]-6-fluoro-3H-quinazolin-4-one;

3-(2-bromo-phenyl)-2-[2-(6-diethylaminomethyl-pyridin-2-yl)-vinyl]-3-3H-quinazolin-4-one;

acetic acid 6-{2-[3-(2-bromo-phenyl)-6-fluoro-4-oxo-3,4-dihydro-quinazolin-2-yl]-vinyl}-pyridin-2-ylmethyl ester;

3-(2-chloro-phenyl)-6-fluoro-2-[2-(6-methoxymethyl-pyridin-2-yl)-vinyl]-3H-quinazolin-4-one;

diethylamino-acetic acid 6-{2-[3-(2-chloro-phenyl)-6-fluoro-4-oxo-3,4-dihydro-quinazolin-2-yl]-vinyl}-pyridin-2-ylmethyl ester;

6-fluoro-3-(2-methyl-pyridin-3-yl)-2-[2-(2-methyl-thiazol-4-yl)-vinyl]-3H-quinazolin-4-one;

3-(2-bromo-phenyl)-6-fluoro-2-[2-(6-hydroxymethyl-pyridin-2-yl)-vinyl]-3H-quinazolin-4-one;

3-(2-chloro-phenyl)-6-fluoro-2-[2-(6-pyrrolidin-1-ylmethyl-pyridin-2-yl)-vinyl]-3H-quinazolin-4-one;

(D) 6-Chloro-3-(2-chloro-phenyl)-2-[2-hydroxy-2-(6-methyl-pyridin-2-yl)-vinyl]-3H-quinazolin-4-one;

2-{2-[3-(2-Chloro-phenyl)-4-oxo-3,4-dihydro-quinazolin-2-yl]-1-hydroxy-vinyl}-nicotinonitrile;

2-{2-[3-(2-Chloro-pyrid-3-yl)-(6-fluoro-4-oxo-3,4-dihydro-quinazolin-2-yl]-1-hydroxy-vinyl}-nicotinonitrile;

2-{2-[6-Chloro-3-(2-methyl-phenyl)-4-oxo-3,4-dihydro-quinazolin-2-yl]-1-hydroxy-vinyl}-nicotinonitrile;

3-(2-Chloro-phenyl)-2-[2-(3-diethylaminomethyl-phenyl)-2hydroxy-ethyl]-6-fluoro-3H-quinazolin-4-one;

3-(2-Chloro-phenyl)-6-fluoro-2-[2-(3-pyrrolidin-1-ylmethyl-phenyl)-2-hydroxy-ethyl]-3H-quinazolin-4-one;

3-(2-Chloro-pyrid-3-yl)-2-[2-(3-diethylaminomethyl-phenyl)-2-hydroxy-ethyl]-6-fluoro-3H-quinazolin-4-one;

2-[2-(3-Diethylaminomethyl-phenyl)-2-hydroxy-ethyl]-6-fluoro-3-(2-fluoro-phenyl)-3H-quinazolin-4-one;

2-[2-(3-Diethylaminomethyl-phenyl)-2-hydroxy-ethyl]-3-(2-fluoro-phenyl)-3H-quinazolin-4-one;

3-(2-chloro-phenyl)-2-[2-(6-diethylaminomethyl-pyridin-2-yl)-2-hydroxy-vinyl]-6fluoro-3H-quinazolin-4-one;

2-{2-[3-(2-Chloro-pyrid-3-yl)-6-fluoro-4-oxo-3,4-dihydro-quinazolin-2-yl]-1-hydroxy-vinyl}-6-methyl-nicotinonitrile;

2-{2-[3-(2-Chloro-phenyl)-4-oxo-3,4-dihydro-quinazolin-2-yl]-1-hydroxy-vinyl}-6-methyl-nicotinonitrile;

2-{2-[6-chloro-phenyl)-4oxo-3,4-dihydro-quinazolin-2-yl]-1-hydroxy-vinyl}-6-methyl-nicotinonitrile;

2-{2-[3-(2-Chloro-phenyl)-6-4-oxo-3,4-dihydro-quinazolin-2-yl]-1-hydroxy-vinyl}-6-fluoro-nicotinonitrile;

2-{2-[3-(2-Chloro-phenyl)-6-fluoro-4-oxo-3,4-dihydro-quinazolin-2-yl]-1-hydroxy-vinyl}-4-fluoro-benzonitrile;

2-{2-[3-(2-Chloro-phenyl)-6-fluoro-4-oxo-3,4-dihydro-quinazolin-2-yl]-1-hydroxy-vinyl}-4-methyl-benzonitrile;

2-{2-[3-(2-Chloro-phenyl)-4-oxo-3,4-dihydro-thieno[3,2-d]pyrimidin-2-yl]-1-hydroxy-vinyl}-6-methyl-nicotinontrile;

2-{2-[3-(2-methyl-phenyl)-4-oxo-3,4-dihydro-thieno[3,2-d]pyrimidin-2-yl]-1-hydroxy-vinyl}-6-methyl-nicotinonitrile;

2-{2-[3-Chloro-pyrid-3yl)-4-oxo-3,4-dihydro-thieno[3,2-d]pyrimidin-2-yl]-1-hydroxy-vinyl}-4-methyl-benzonitrile;

2-{2-[3-(2-Chloro-phenyl)-4-oxo-3,4-dihydro-thieno[3,2-d]pyrimidin-2-yl]-1-hydroxy-vinyl}-4-fluoro-benzonitrile;

2-{2-[3-(2-Fluoro-phenyl)-4-oxo-3,4-dihydro-thieno[3,2-d]pyrimidin-2-yl]-1-hydroxy-vinyl}-4-methyl-benzonitrile;

2-{2-[3-(2-Chloro-phenyl)-4-oxo-3,4-dihydro-thieno[3,2-d]-pyrimidin-2-yl]-1-hydroxy-vinyl}-benzonitrile; and, 2-{2-[3-(2-Chloro-pyrid-3yl)-4-oxo-3,4-dihydro-thieno[3,2-d]-pyrimidin-2-yl]-1-hydroxy-vinyl}-benzonitrile;

3-(2-chloro-phenyl)-6-fluoro-2-[2-hydroxy-2-(2-methyl-thiazol-4-yl)-vinyl]-3H-quinazolin-4-one;

3-(2-chloro-phenyl)-6-fluoro-2-[2-hydroxy-2-(6-methyl-pyridin-2-yl)-vinyl]-3H-quinazolin-4-one;

2-{2-[3-(2-chloro-phenyl)-6-fluoro-4-oxo-3,4-dihydro-quinazolin-2-yl]-1-hydroxy-vinyl}-6-methyl-nicotinonitrile;

2-{2-[3-(2-chloro-phenyl)-6-fluoro-4-oxo-3,4-dihydro-quinazolin-2-yl]-1-hydroxy-vinyl}-nicotinonitrile;

2-{2-[3-(2-chloro-phenyl)-6-fluoro-4-oxo-3,4-dihydro-quinazolin-2-yl]-1-hydroxy-vinyl}-benzonitrile;

2-{2-[3-(2-chloro-pyridin-3yl)-6-fluoro-4-oxo-3,4-dihydro-quinazolin-2-yl]-1-hydroxy-vinyl}-6-methyl-nicotinonitrile;

3-(2-chloro-phenyl)-6-fluoro-2-(2-hydroxy-2-pyridin-(2-yl-vinyl)-3H-quinazolin-4-one;

2-{2-[6-fluoro-3-(2-methyl-pyridin-3-yl)-4-oxo-3,4-dihydro-quinazolin-2-yl]-1-hydroxy-vinyl}-benzonitrile;

2-{2-[3-(2-chloro-pyridin-3yl)-6-fluoro-4-oxo-3,4-dihydro-quinazolin-2-yl]-1-hydroxy-vinyl}-benzonitrile;

3-(2-chloro-phenyl)-6-fluoro-2-[2-(2-fluoro-phenyl)-2-hydroxy-ethyl]-3H-quinazolin-4-one;

(E) 3-(2-chloro-phenyl)-6-fluoro-2-[(pyridin-2-ylmethyl-amino]-3H-quinazolin-4-one;

6-fluoro-3-(2-methyl-phenyl)-2-[(pyridin-2-ylmethyl-amino]-3H-quinazolin-4-one;

3-(2-chloro-phenyl)-6-fluoro-2-[(2-fluorophenyl-methyl)-amino]-3H-quinazolin-4-one;

3-(2-chloro-phenyl)-2-[(2-cyanophenyl-methyl)-amino]-6-fluoro-3H-quinazolin-4-one;

3-(2-chloro-phenyl)-2-[(6-diethylaminomethylpyridin-2-ylmethyl)-amino]-6-fluoro-3H-quinazolin-4-one;

3-(2-chloro-phenyl)-6-fluoro-2-[(6-pyrrolidin-1-ylmethyl-pyridin-2-ylmethyl)-amino]-3H-quinazolin-4-one;

3-(2-chloro-phenyl)-2[(3-pyrrolidin-1-ylmethyl-phenylamino)-methyl]-3H-thieno[3,2-d]pyrimidin-4-one;

3-(2-methyl-phenyl)-2-[(3-pyrrolidin-1-ylmethyl-phenylamino)-methyl]-3H-thieno[3,2-d]pyrimidin-4-one;

3-(2-chloro-phenyl)-2-[(2-fluoro-phenylamino)-methyl]-3H-thieno[3,2-d]pyrimidin-4-one;

3-(2-chloro-pyrid-3-yl)-2-[(3-pyrrolidin-1-ylmethyl-phenylamino)-methyl]-3H-thieno[3,2-d]pyrimidin-4-one;

2-{[3-(2-chloro-pyrid-3-yl)-4-oxo-3,4-dihydro-thieno[3,2-d]pyrimidin-2-ylmethyl]-amino}-benzonitrile;

3-(2-chloro-phenyl)-2-[(3-pyrrolidin-1-ylmethyl-phenylamino)-methyl]-3H-quinazolin-4-one;

6-chloro-3-(2-chloro-phenyl)-2-[(3-pyrrolidin-1-ylmethyl-phenylamino)-methyl]-3H-quinazolin-4-one;

6-chloro-3-(2-chloro-phenyl)-2-[(3-diethylaminomethyl-phenylamino)-methyl]-3H-quinazolin-4-one;

3-(2-chloro-pyrid-3-yl)-2-[(3-pyrrolidin-1-ylmethyl-phenylamino)-methyl]-3H-thieno[3,2-d]pyrimidin-4-one;

6-chloro-3-(2-chloro-pyrid-3-yl)-2-[(3-diethylaminomethyl-phenylamino)-methyl]-3H-quinazolin-4-one;

6-chloro-3-(2-trifluoromethyl-phenyl)-2-[(3-diethylaminomethyl-phenylamino)-methyl]-3H-quinazolin-4-one;

2-{[3-(2-chloro-pyridin-3-yl)-4-oxo-3,4-dihydro-quinazolin-2-ylmethyl]-amino}-benzonitrile;

2-{[3-(2-methyl-pyridin-3-yl)-4-oxo-3,4-dihydro-quinazolin-2-ylmethyl]-amino}-benzonitrile;

2-{[6-fluoro-3-(2-methyl-phenyl)-4-oxo-3,4-dihydro-quinazolin-2-ylmethyl]-amino}-nicotinonitrile;

2-{[3-(2-chloro-phenyl)-4-oxo-3,4-dihydro-quinazolin-2-ylmethyl]-amino}-nicotinonitrile;

2-{[3-(2-chloro-pyridin-3-yl)-6-fluoro-4-oxo-3,4-dihydro-quinazolin-2-ylmethyl]-amino}-benzonitrile;

3-{[3-(2-chloro-phenyl)-6-fluoro-4-oxo-3,4-dihydro-quinazolin-2-ylmethyl]-amino}-benzonitrile;

3-(2-chloro-phenyl)-2-[(3-diethylaminomethyl-phenylamino)-methyl]-6-fluoro-3H-quinazolin-4-one;

3-(2-chloro-phenyl)-6-fluoro-2(pyrimidin-2-ylaminomethyl)-3H-quinazolin-4-one;

3-(2-chloro-pyridin-3-yl)-6-fluoro-2-(m-tolylamino-methyl)-3H-quinazolin-4-one;

3-(2-chloro-pyridin-3-yl)-6-fluoro-2-[(6-methyl-pyridin-2-ylamino)-methyl]-3H-quinazolin-4-one;

3-(2-chloro-phenyl)-6-fluoro-2-(pyridin-2-ylaminomethyl)-3H-quinazolin-4-one;

3-(2-chloro-pyridin-3-yl)-6-fluoro-2-[(3-pyrrolidin-1-ylmethyl-phenylamino)-methyl]-3H-quinazolin-4-one;

6-fluoro-3-(2-methyl-pyridin-3-yl)-2-[(3-pyrrolidin-1-ylmethyl-phenylamino)-methyl]-3H-quinazolin-4-one;

3-(2-chloro-phenyl)-6-fluoro-2-[(2-fluoro-benzylamino)-methyl]-3H-quinazolin-4-one;

N-(3-{[3-(2-chloro-phenyl)-6-fluoro-4-oxo-3,4-dihydro-quinazolin-2-ylmethyl]-amino}-phenyl)-acetamide;

3-(2-chloro-phenyl)-6-fluoro-2-[(3-pyrrolidin-1-ylmethyl-phenylamino)-methyl]-3H-quinazolin-4-one;

2-{[3-(2-chloro-phenyl)-6-fluoro-4-oxo-3,4-dihydro-quinazolin-2-ylmethyl]-amino}-nicotinonitrile;

3-(2-chloro-pyridin-3-yl)-6-fluoro-2-[(2-fluoro-phenylamino)-methyl]-3H-quinazolin-4-one;

3-(2-chloro-phenyl)-6-fluoro-2-[(2-fluoro-phenylamino)-methyl]-3H-quinazolin-4-one;

3-(2-chloro-phenyl)-6-fluoro-2-[(6-methyl-pyridin-2-ylamino)-methyl]-3H-quinazolin-4-one; and, (F) an atropisomer of the formula

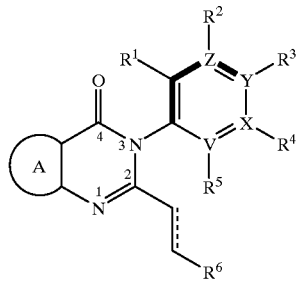

I wherein either V, X, Y and Z are all carbon or one of them is nitrogen and the others are carbon;

each of $R^1$, $R^2$, $R^3$, $R^4$ and $R^5$ is selected, independently, from hydrogen, halogen, $(C_1–C_6)$alkyl, trifluoromethyl, cyano, $(C_1–C_6)$alkoxy, $(C_1–C_6)$alkylthio and $C(=O)\text{-}0\text{-}(C_1–C_6)$alkyl, with the proviso that: (a) $R^1$ can not be the same as $R^5$, when each of V, X and Z is carbon; (b) at least one of $R^1$ and $R^5$ must be other than hydrogen; and (c) when V, X, Y or Z is nitrogen, then $R^5$, $R^4$, $R^3$ or $R^2$ respectively, is absent;

ring A is a fused heteroaromatic ring, wherein said heteroaromatic ring is a 5 or 6 membered heteroaromatic ring, wherein said 6 membered heteroaromatic ring, taken together with the carbon atoms common to both rings of the bicyclic system, has the formula

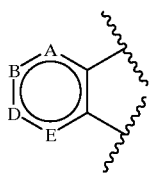

and wherein said 5 membered heteroaromatic ring, taken together with the carbon atoms common to both rings of the bicyclic system, has the formula

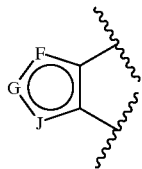

wherein said ring positions "A", "B", "D" and "E" may be independently selected from carbon or nitrogen;

wherein said ring positions "F", "G" and "J" may be independently selected from carbon, nitrogen, oxygen or sulfur, with the proviso that: (a) if more than two of "F", "G" or "J" is a heteroatom then said 5 membered heteroaromatic ring is selected from the group consisting of (1,2,3)-triazole, (1,2,3)-thiadiazole, (1,2,5)-thiadiazole, and (1,2,5)-oxadiazole; and (b) if two of "F", "G" or "J" are heteroatoms, only one of said heteroatoms may be oxygen or sulfur;

wherein said fused heteroaromatic rings may optionally be independently substituted on any of the carbon or nitrogen atoms capable of forming an additional bond with a substituent selected from hydrogen, $(C_1-C_6)$alkyl, halogen, trifluoromethyl, amino-$(CH_2)_n$-, $(C_1-C_6)$alkylamino-$(CH_2)_n$-, di$(C_1-C_6)$alkyl-amino-$(CH_2)_n$-, $(C_1-C_6)$alkoxy, hydroxy $(C_1-C_6)$alkyl, $(C_1-C_6)$alkyl-O—$(C_1-C_6)$alkyl-, —CN, $(C_1-C_6)$alkyl-CO—O—$(C_1-C_6)$alkyl-, $(C_1-C_6)$alkyl-O—CO—O—$(C_1-C_6)$alkyl, $(C_1-C_6)$alkyl-CO—O—, hydroxy, —$NO_2$, $R^{15}$—C(=O)—, $R^{15}$—O—C(=O)—, di$(C_1-C_6)$alkyl-N—C(=O)—, $(C_3-C_7)$cycloalkyl, and $R^{15}$—NH—C(=O)—, and phenyl optionally substituted with halo, $(C_1-C_6)$alkyl, —CN, or —$CF_3$;

$R^6$ is phenyl of the formula $Ph^1$ or a five or six membered heterocycle, wherein said 6-membered heterocycle has the formula

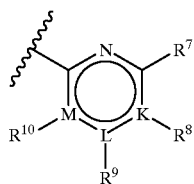

wherein "N" is nitrogen; wherein said ring positions "K", "L" and "M" may be independently selected from carbon or nitrogen, with the proviso that only one of "K", "L" or "M" can be nitrogen;

wherein said five membered heterocycle has the formula

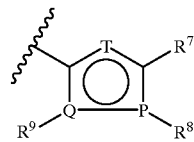

wherein said ring positions "P," "Q" and "T" may be independently selected from carbon, nitrogen, oxygen or sulfur, with the proviso that only one of "P," "Q" or "T" can be oxygen or sulfur and at least one of "P," "Q" or "T" must be a heteroatom;

wherein said $Ph^1$ is a group of the formula

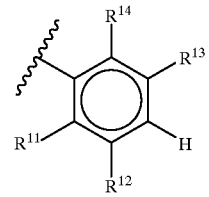

wherein each $R^{15}$ is, independently, hydrogen or $(C_1-C_6)$alkyl;

each of $R^9$, $R^{10}$ and $R^{11}$ is selected, independently, from hydrogen, $(C_1-C_6)$alkyl optionally substituted with one to three halogen atoms, halo, $CF_3$, $(C_1-C_6)$alkoxy optionally substituted with one to three halogen atoms, $(C_1-C_6)$alkylthiol, $R^{16}$O—$(CH_2)_p$—, $(C_1-C_6)$alkyl—NH—$(CH_2)_p$—, di$(C_1-C_6)$alkyl—N—$(CH_2)_p$—, $(C_3-C_7)$cycloalkyl—NH—$(CH_2)_p$—, $H_2N$—(C=O)—$(CH_2)_p$—, $(C_1-C_6)$alkyl—HN—(C=O)—$(CH_2)_p$—, di$(C_1-C_6)$alkyl—N—(C=O)—$(CH_2)_p$—, $(C_3-C_7)$cycloalkyl—NH—(C=O)—$(CH_2)_p$—, $R^{16}$O—(C=O)—$(CH_2)_p$—, $(C_1-C_6)$alkyl—(O=C)—O—$(C_1-C_6)$alkyl-, $(C_1-C_6)$alkyl—O—(O=C)—O—$(C_1-C_6)$-alkyl-, $(C_1-C_6)$alkyl—(O=C)—O—, $(C_1-C_6)$alkyl—(O=C)—NH—$(CH_2)_p$—, H(O=C)—NH—$(CH_2)_p$—, $(C_1-C_6)$alkyl—(O=C)—N—[$(C_1-C_6)$alkyl]$(CH_2)_p$—, H(O=C)—N—[$(C_1-C_6)$alkyl]$(CH_2)_p$—, hydroxy, H—C(=O)—$(CH_2)_p$—, $(C_1-C_6)$alkyl—C(=O)—, $(C_1-C_6)$alkyl—O—C(=O)—, $R^{15}$—$(CH_2)_p$—O—C(=O)—, amino-$(CH_2)_p$—, hydroxy-$(C_1-C_6)$alkyl—, $(C_1-C_6)$alkyl—O—$(C_1-C_6)$alkyl- and cyano;

each of $R^7$, $R^{12}$ and $R^{13}$ is selected, independently, from hydrogen, $(C_1-C_6)$alkyl optionally substituted with one to three halogen atoms, halogen, $CF_3$, $(C_1-C_6)$alkoxy optionally substituted with one to three halogen atoms, $(C_1-C_6)$alkylthiol, $R^{16}$O—$(CH_2)_p$—, $(C_1-C_6)$alkyl—NH—$(CH_2)_p$—, di$(C_1-C_6)$alkyl—N—$(CH_2)_p$—, $(C_3-C_7)$cycloalkyl—NH—$(CH_2)_p$—, $H_2N$—(C=O)—$(CH_2)_p$—, $(C_1-C_6)$alkyl—HN—(C=O)—$(CH_2)_p$—, di$(C_1-C_6)$alkyl—N—(C=O)—$(CH_2)_p$—, $(C_3-C_7)$cycloalkyl—NH—(C=O)—$(CH_2)_p$—, $R^{16}$O—(C=O)—$(CH_2)_p$—, $(C_1-C_6)$alkyl—(O=C)—O—$(C_1-C_6)$alkyl-, $(C_1-C_6)$alkyl—O—(O=C)—O—$(C_1-C_6)$— alkyl-, $(C_1-C_6)$alkyl—(O=C)—O—, $(C_1-C_6)$alkyl—(O=C)—NH—$(CH_2)_p$—, H(O=C)—NH—$(CH_2)_p$—, $(C_1-C_6)$alkyl—(O=C)—N—[$(C_1-C_6)$alkyl]$(CH_2)_p$, H(O=C)—N—[$(C_1-C_6)$alkyl]$(CH_2)_p$—, hydroxy, H—C(=O)—$(CH_2)_p$—, $(C_1-C_6)$alkyl—C(=O)—, $(C_1-C_6)$alkyl—O—C(=O)—, $R^{15}$—$(CH_2)_p$—O—C(=O)—, amino-$(CH_2)_p$—, hydroxy-$(C_1-C_6)$alkyl—, $(C_1-C_6)$alkyl—O—$(C_1-C_6)$alkyl—, —CHO and cyano;

each $R^{14}$ is, independently, hydrogen or halogen;

each $R^{16}$ is, independently, hydrogen, $(C_1-C_6)$alkyl, $(C_1-C_6)$alkyl-(C=O)—, $(C_1-C_6)$alkyl-O—(C=O)—, $(C_1-C_6)$alkyl—NH—(C=O)—, or di$(C_1-C_6)$alkyl—N—(C=O)—;

each is hydrogen, cyano, $(C_1-C_6)$alkyl, halogen, trifluoromethyl, —CHO or $(C_1-C_6)$alkoxy;

n is an integer from zero to 3;

p is an integer from zero to 3; and wherein the dashed bond represented an optional double bond;

with the proviso that when $R^{11}$ is hydrogen, one of $R^{13}$ and $R^{14}$ is other than hydrogen.

In a specific embodiment of the above method, said dopamine agonist therapy is therapy comprising the administration of L-dopa or L-dopa in combination with an inhibitor of peripheral dopadecarboxylase such as carbidopa or benserazide.

In another specific embodiment of the above method, said compound is a compound of group (A) or a pharmaceutically acceptable salt thereof.

In another specific embodiment of the above method, said compound is a compound of group (B) or a pharmaceutically acceptable salt thereof.

This invention also relates to a method of treating dyskinesias associated with dopamine agonist therapy in a mammal, such as a human, which comprises administering to said mammal an AMPA receptor antagonizing effective amount of a compound within group (A), (B), (C), (D), (E), or (F), or a pharmaceutically acceptable salt of said compound, wherein groups (A), (B), (C), (D), (E), and (F) are as defined above.

This invention also relates to a method of treating dyskinesias associated with dopamine agonist therapy in a mammal, such as a human, which comprises administering to said mammal an AMPA receptor antagonizing effective amount of a compound selected from the group consisting of an AMPA receptor antagonist referred to in PCT international application publication number WO 97/19066; the compounds "NS-1201" or "NS-479" developed or marketed by Neurosearch (Denmark); the compound "LY-311446" (2-amino-3-(2-(3-(1H-tetrazol-5-yl)phenoxy)phenyl) propionic acid), "LY-300164" (7-acetyl-5-(4-aminophenyl)-8(R)-methyl-8,9-dihydro-7H-1,2-dioxolo(4,5-H)(2,3) benzodiazepine), "LY-293606", "LY-293558", or "GYKI-53655" of Eli Lilly (United States) or any AMPA antagonist referred to in 20th CINP (Melbourne), 1996, Abs S-40-1; the compound "NNC-07-0775" of Novo Nordisk (Denmark) or any AMPA antagonist referred to in PCT international publication number WO 96/15100; the compound "SYM-2206" (4-(aminophenyl)-1-methyl-6,7-(methylenedioxy)-N-butyl-1,2-dihydrophthalazine-2-carboxamide) of Symphony Pharmaceuticals (United States) or any AMPA antagonist referred to in Journal of Medicianl Chemistry, 1996, 39, 343; the compound "A-17625" (6,7-dichloro-2 (1H)-oxoquinoline-3-phosphonic acid) of Servier (France) or any AMPA antagonist referred to in Journal of Medicinal Chemistry, 1996, 39, 197; 2-carboxy-1-methyl-7-trifluoromethylimidazo(1,2-a)quinoxalin-4(5H)-one or any AMPA antagonist referred to in PCT international publication numbers WO 95/21842, WO 96/08492, and WO 96/08493; 6-(4- pyridinyl)-1H-1,2,3-triazolo(4,5-a) pyrimidin-4(5H)-one or any AMPA antagonist referred to in Journal of Medicinal Chemistry 1995, 38, 587; any AMPA antagonist referred to in PCT international publication numbers WO 94/26747, WO 95/19346, WO 95/12594, WO 95/02601, WO 95/26342, WO 95/26349, WO 95/26350, WO 95/26351, WO 95/26352, WO 96/31511, and WO 95/02602; 2-amino-3-(3-hydroxy-5-(2-thienyl)isoxazol-4-yl)propionic acid or any AMPA antagonist referred to in PCT international publication number WO 95/12587; the compound "SYM-2250" of Symphony Pharmaceuticals (United States); the compound "S-18986" of Servier (France) or any AMPA antagonist referred to in 13th Int. Symp. Med. Chem. (Paris), 1994, Abs P29; the compound "NNC-07-9202 of Warner-Lambert (United States) or any AMPA antagonist referred to in 208th ACS (Washington, D.C.), 1994, Abs MEDI 170; the compound "IDRA-21" (7-chloro-3-methyl-3,4-dihydro-2H-1,2,4-benzothiadiazine-5,5-dioxide) or any AMPA antagonist referred to in Soc. Neurosci. Abs (Washington, D.C.), 1993, Abs 124.7 and 124.8; the compound "NS-409" of Warner-Lambert (United States) or any AMPA antagonist referred to in J. Med. Chem. 1995, 38, 3720 or PCT international publication numbers WO 96/08494 and WO 96/08495; the compound "NS-393" of Neurosearch (Denmark); the compounds "SYM-2101", "SYM-2007" and "SYM-2057" of Symphony Pharmaceuticals (United States); the compound "AMPAlex" (1-(1,3-benzodioxolo-5-ylcarbonyl)piperidine) of Cortex Pharmaceuticals (United States) or any AMPA antagonist referred to in Scrip, 1995, 2088/9, 14 and Scrip, 1996, 2187, 21 or in PCT international publication number WO 96/38414; the compounds "LY-293558", "LY-215490", and decahydro-6-(2-(1H-tetrazol-5-yl)ethyl)-3-isoquinolinecarboxylic acid (CAS registry no. 154652-83-2) or any AMPA antagonist referred to in J. Med. Chem., 1993, 36, 2046; the compound "YM-90K" (1,4-dihydro-6-(1H-imidazol-1-yl)-7-nitro-2,3-quinoxalinedione monohydrochloride (CAS registry no. 154164-30-4 or any AMPA antagonist referred to in Scrip, 1994, 1972, 14 or PCT international publication number WO 96/10023; the compound "aloracetam" (N-(2-(3-formyl-2,5-dimethyl-1H-pyrrol-1-yl)ethyl)-acetamide)(CAS registry no. 119610-26-3) or any AMPA antagonist referred to in European Patent 287988; the compound "NS-257" of Warner-Lambert; the compound "NNC-07-9202 of Novo Nordisk (Denmark) or any AMPA antagonist referred to in European Patent 283959 and Science, 1988, 241, 701; and the compound "aniracetam" of Roche (Switzerland) or 1-(4-methoxybenzyl)-2-pyrrolidinone (CAS registry no. 72432-10-1) or any AMPA antagonist referred to in European Patent 5143.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "dyskinesia(s)", as used herein, unless otherwise indicated, means any abnormal or uncontrollable movement including, but not limited to, chorea, tremor, ballism, dystonia, athetosis, myoclonus and tic.

The term or phrase "dopamine agonist therapy", as used herein, unless otherwise indicated, means any therapy that increases dopamine receptor stimulation, including, but not limited to, therapies that directly stimulate dopamine receptors (such as bromocriptine) and therapies that increase the levels of dopamine (such as L-dopa or drugs which inhibit dopamine metabolism). Dopamine agonist therapies include, but are not limited to, therapies comprising the administration of one or more of the following agents: L-dopa, L-dopa in combination with an l-dopa decarboxylase inhibitor such as carbidopa or benserazide, bromocriptine, dihydroergocryptine, etisulergine, AF-14, alaptide, pergolide, piribedil, dopamine D1 receptor agonists such as A-68939, A-77636, dihydrexine, and SKF-38393; dopamine D2 receptor agonists such as carbergoline, lisuride, N-0434, naxagolide, PD-118440, pramipexole, quinpirole and ropinirole; dopamine/β-adrenergic receptor agonists such as DPDMS and dopexamine; dopamine/5-HT uptake inhibitor/5-HT-1A agonists such as roxindole; dopamine/opiate receptor agonists such as NIH-10494; α2-adrenergic antagonist/dopamine agonists such as terguride; α2-adrenergic antagonist/dopamine D2 agonists such as ergolines and talipexole; dopamine uptake inhibitors such as GBR-12909, GBR-13069, GYKI-52895, and NS-2141; monoamine oxidase-B inhibitors such as selegiline, N-(2-butyl)-N-methylpropargylamine, N-methyl-N-(2-pentyl)propargylamine, AGN-1133, ergot derivatives, lazabemide, LU-53439, MD-280040 and mofegiline; and COMT inhibitors such as CGP-28014, entacapone and tolcapone. Dopamine agonist therapy, as referred to in the present invention, is used in the treatment of a central nervous system disorder such as, but not limited to, Parkinson's disease.

The term or phrase "dyskinesia associated with dopamine agonist therapy", as used herein, unless otherwise indicated, means any dyskinesia which accompanies, or follows in the course of, dopamine agonist therapy, or which is caused by, related to, or exacerbated by dopamine agonist therapy, wherein dyskinesia and dopamine agonist therapy are as defined above.

In the compounds of groups (A) and (B), referred to above, the designation "(S)" appearing at the beginning of each compound refers to the configuration of each compound as an atropisomer. The compounds of group (F) are also atropisomers, and the compounds of groups (C), (D) and (E) include atropisomers. Atropisomers are conformational isomers that occur when rotation about a single bond in the molecule is prevented or greatly slowed as a result of steric interactions with other parts of the molecule and the substituents at both ends of the single bond are unsymmetrical. A detailed account of atropisomers can be found in Jerry March, Advanced Organic Chemistry, 101–102 (4th ed. 1992) and in Oki, Top. Stereochem., 14, 1–81 (1983). Each compound within groups (A), (B) and (F) has the same (S) configuration as an atropisomer. This configuration is described in United States provisional patent applications numbers 60/038905 (filed Feb. 28, 1997) and 60/038540 (filed Feb. 28, 1997), both of which are referred to above. This configuration may be illustrated with respect to the first compound listed in group (A) which is (S)-3-(2-chloro-phenyl)-2-[2-(5-diethylaminomethyl-2-fluoro-phenyl)-vinyl]-6-fluoro-3H-quinazolin-4-one. Below, both atropisomeric configurations are illustrated.

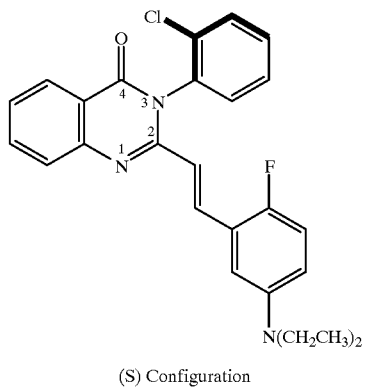

(S) Configuration

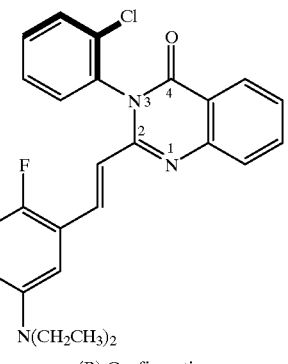

(R) Configuration

In the above structures, the bold lines indicate that the bolded atoms of the 2-chloro-phenyl group are sterically restricted so as to exist above the plane of the quinazolinone ring. This steric restriction is due to a rotational energy barrier preventing free rotation about the single bond connecting the nitrogen at position 3 of the quinazolinone ring to the 2-chloro-phenyl group. The above (S) configuration is also illustrated in formula I of group (F). The other compounds of groups (A), (B) and (F) are all atropisomers having an (S) configuration analogous to the structure labeled "(S) Configuration" illustrated above. The compounds of groups (C), (D), and (E) also exist, and may be isolated as, atropisomers having (S) and (R) configurations corresponding to the (S) and (R) configurations illustrated above.

In addition to the atropisomerism referred to above, the compounds of groups (A), (B), (C), (D), (E), and (F) may have chiral centers and therefore may exist in different enantiomeric and diastereomic forms. This invention relates to all optical isomers and all stereoisomers of compounds of groups (A), (B), (C), (D), and (F), and mixtures thereof, and to all methods of treatment defined above that contain or employ them, respectively.

The method of the present invention also relates to the use of pharmaceutically acceptable acid addition salts of the compounds of groups (A), (B), (C), (D), (E), and (F). The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of the compounds of groups (A), (B), (C), (D), (E), and (F). The chemical bases that may be used as reagents to prepare pharmaceutically acceptable base salts of those compounds of groups (A), (B),(C), (D),(E), and (F) that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine (meglumine), and the lower alkanolammonium and other base salts of pharmaceutically acceptable organic amines.

DETAILED DESCRIPTION OF THE INVENTION

The compounds of groups (A), (B), (C), (D), (E), and (F) are readily prepared. The compounds of group (A) can be prepared and separated as atropisomers according to one or more methods referred to in United States provisional patent application number 60/038905 (filed Feb. 28, 1997), referred to above. The compounds of group (B) can be prepared and separated as atropisomers according to one or more methods referred to in United States provisional patent application number 60/038540 (filed Feb. 28, 1997), referred to above. The compounds of group (C) can be prepared according to one or more methods referred to in PCT international application number PCT/IB97/00134 (filed Feb. 17, 1997), referred to above. The compounds of group (D) can be prepared according to one or more methods referred to in United States provisional patent application number 60/049083 (filed Jun. 9, 1997), referred to above. The compounds of group (E) can be prepared according to one or more methods referred to in United States provisional patent application number 60/049082 (filed Jun. 9, 1997), referred to above, and United States provisional patent application entitled "Quinazolin-4-one AMPA Antagonists", filed Jul. 21, 1997 with Bertrand L. Chenard, Willard M. Welch, and Anthony R. Reinhold named as inventors, referred to above. The compounds of group (F) can be prepared according to one or more methods referred to in United States provisional patent application entitled "Novel Atropisomrs Of 2,3-Disubstituted-(5,6)-Heteroarylfused-Pyrimidin-4-ones" filed Aug. 27, 1997 with Bertrand L. Chenard and Willard M. Welch named as inventors, referred to above.

The compounds of groups (A), (B), (C), (D), (E), and (F), referred to above, which are basic in nature are capable of forming a wide variety of different salts with various inorganic and organic acids. Although such salts must be pharmaceutically acceptable for administration to animals, it is often desirable in practice to initially isolate a compound of group (A), (B), (C), (D), (E), or (F) from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of the method of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of groups (A), (B), (C), (D), (E) and (F) are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of groups (A), (B), (C), (D), (E), and (F) which are acidic in nature are capable of forming base salts with various pharmacologically acceptable cations. Examples of such salts include the alkali metal or alkaline-earth metal salts and particular, the sodium and potassium salts. These salts are all prepared by conventional techniques. The chemical bases which are used as reagents to prepare the pharmaceutically acceptable base salts of this invention are those which form non-toxic base salts with the herein described acidic compounds of groups (A), (B), (C), (D), (E), and (F). These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction of maximum product of yields of the desired final product.

The in vitro and in vivo activity of the compounds of groups (A), (B), (C), (D), (E), and (F) for AMPA receptor antagonism can be determined by methods available to one of ordinary skill in the art. One method for determining the activity of the compounds of groups (A), (B), (C), (D), (E), and (F) is by blockage of AMPA receptor activation-induced $^{45}Ca^{2+}$ uptake into neurons. A specific method for determining blockage of AMPA receptor activation-induced $^{45}Ca^{2+}$ uptake into neurons is described below.

Neuronal Primary Cultures

Primary cultures of rat cerebellar granule neurons are prepared as described by Parks, T. N., Artman, L. D., Alasti, N., and Nemeth, E. F., *Modulation Of N-Methyl-D-Aspartate Receptor-Mediated Increases In Cytosolic Calcium in Cultured Rat Cerebellar Granule Cells, Brain Res.* 552, 13–22 (1991). According to this method, cerebella are removed from 8 day old CD rats, minced into 1 mm pieces and incubated for 15 minutes at 37° C. in calcium-magnesium free Tyrode's solution containing 0.1% trypsin. The tissue is then triturated using a fine bore Pasteur pipette. The cell suspension is plated onto poly-D-lysine coated 96-well tissue culture plates at $10^5$ cells per well. Medium consists of Minimal Essential Medium (MEM), with Earle's salts, 10% heat inactivated Fetal Bovine Serum, 2 mM L-glutamine, 21 mM glucose, Penicillin-Streptomycin (100 units per ml) and 25 mM KCl. After 24 hours, the medium is replaced with fresh medium containing 10 μM cytosine arabinoside to inhibit cell division. Cultures are used 6 to 8 days later.

AMPA Receptor Activation-induced $^{45}Ca^{2+}$ Uptake

The effects of drugs on AMPA receptor activation-induced $^{45}Ca^{2+}$ uptake can be examined in rat cerebellar granule cell cultures prepared as described above. Cultures in 96 well plates are preincubated for approximately 3 hours in serum free medium and then for 10 minutes in a $Mg^{2+}$-free balanced salt solution (in mM: 120 NaCl, 5 KCl, 0.33 $NaH_2PO_4$ 1.8 $CaCl_2$, 22.0 glucose and 10.0 HEPES at pH 7.4) containing 0.5 mM DTT, 10 μM glycine and drugs at 2×final concentration. The reaction is started by rapid addition of an equal volume of the balanced salt solution containing 100 μM of the AMPA receptor agonist kainic acid and $^{45}Ca^{2+}$ (final specific activity 250 Ci/mmol). After 10 minutes at 25° C., the reaction is stopped by aspirating the $^{45}Ca^{2+}$-containing solution and washing the cells 5×in an ice cold balanced salt solution containing no added calcium and 0.5 mM EDTA. Cells are then lysed by overnight incubation in 0.1% Triton-x100 and radioactivity in the lysate is then determined. all compounds of groups (A), (B), (C), (D), (E), and (F), referred to above, at concentrations of 0.5 μM or less inhibited the AMPA receptor activation-induced $^{45}Ca^{2+}$ uptake by 50% or more.

The following procedure may be used to assess the efficacy of the compounds of groups groups (A), (B), (C), (D), (E), and (F) in the treatment of dyskinesias associated with dopamine agonist therapy in the treatment of Parkinson's disease. Aged, female rhesus monkeys are rendered Parkinsonian as follows. Each monkey is first infused with 0.4 mg/kg MPTP (1-methyl-4-phenyl-1,2,3,6-tetrahydropyridine) via the right internal carotid artery. After being evaluated behaviorally for 3 to 6 weeks and being judged to have stable unilateral deficits, the animals receive a second MPTP injection via the left internal carotid artery. Monkeys lesioned according to this protocol have been shown to have stable, bilateral deficits that are responsive to L-dopa and apomorphine. Once the monkeys are Parkinsonian, dyskinesias are induced over a period of approximately 3 to 6 weeks by treating the monkeys twice daily with subcutaneous injections of PHNO ((+)-4-propyl-9-hydroxynaphthoxazine) (a dopamine agonist). Dyskinesias are assessed 30 minutes after PHNO injection and every 30 minutes for the next 120 minutes (5 measurements) taking into account the following: type of dyskinesia (chorea, dystonia); intensity (0=absent; 1=mild; 2=moderate; 3=severe); and topography (arm, leg, trunk, generalized). The overall score (0–3) is averaged over the 5 measurements. Scoring is performed blindly from coded videotapes. A compound of group (A), (B), (C), (D), (E), or (F) is then administered together with the dopamine agonist at dosages ranging from 0.05 mg/kg to 1 mg/kg.

Pharmaceutical compositions for use in the method of the present invention may be prepared according to methods familiar to those skilled in the art. For example, pharmaceutical compositions containing a compound of group (A), (B), (C), (D), (E), or (F), or a pharmaceutically acceptable salt thereof (hereinafter the "active compound(s)") may be formulated in a conventional manner using one or more pharmaceutically acceptable carriers. Thus, the active compounds may be formulated for oral, buccal, intranasal, parenteral (e.g., intravenous, intramuscular or subcutaneous), transdermal (e.g., patch, ointment, cream or iontophoresis), or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the pharmaceutical composition may take the form of tablets or lozenges formulated in conventional manner.

The active compounds may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds may also be formulated in rectal compositions such as suppositories or retention enemas, e.g., containing conventional suppository bases such as cocoa butter or other glycerides.

For intranasal administration or administration by inhalation, the active compounds are conveniently delivered in the form of a solution or suspension from a pump spray container that is squeezed or pumped by the patient or as an aerosal spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of an active compound and a suitable powder base such as lactose or starch.

A proposed dose of the active compounds for use in the method of the present invention for oral, parenteral or buccal administration to the average adult human requiring treatment is 0.01 to 100 mg/kg of the active ingredient per unit dose which could be administered, for example, 1 to 4 times per day.

Aerosol formulations for use in the method of the present invention in the treatment of an average adult human are preferably arranged so that each metered dose or "puff" of aerosol contains 20 μg to 1000 μg of the active compound. The overall daily dose with an aerosol will be within the range 100 μg to 10 mg. Administration may be several times daily, for example 2, 3, 4 or 8 times, giving for example, 1, 2 or 3 doses each time.

For transdermal administration the composition may take the form of patches, creams, ointments or iontophoresis formulated in conventional manner such as described in U.S. Pat. Nos. 5,004,610 and 5,364,630, issued Apr. 2, 1991 and Nov. 15, 1994 respectively.

What is claimed is:

1. A method of treating dyskinesia associated with dopamine agonist therapy in a mammal which comprises administering to said mammal an amount of a compound within group (A), (B), (C), (D), (E), or (F), or a pharmaceutically acceptable salt of said compound, that is effective in treating said dyskinesia, wherein groups (A), (B), (C), (D), (E), and (F) are defined as follows:

(A) (S)-3-(2-chloro-phenyl)-2-[2-(5-diethylaminomethyl-2-fluoro-phenyl)-vinyl]-6-fluoro-3H-quinazolin-4-one;

(S)-3-(2-chloro-phenyl)-2-[2-(6-diethylaminomethyl-pyridin-2-yl)-vinyl]-6-fluoro-3H-quinazolin-4-one;

(S)-3-(2-chloro-phenyl)-2-[2-(4-diethylaminomethyl-pyridin-2-yl)-vinyl]-6-fluoro-3H-quinazolin-4-one;

(S)-3-(2-chloro-phenyl)-2-[2-(6-ethylaminomethyl-pyridin-2-yl)-vinyl]-6-fluoro-3H-quinazolin-4-one;

(S)-3-(2-bromo-phenyl)-2-[2-(6-diethylaminomethyl-pyridin-2-yl)-vinyl]-6-fluoro-3H-quinazolin-4-one;

(S)-3-(2-chloro-phenyl)-6-fluoro-2-[2-(6-methoxymethyl-pyridin-2-yl)-vinyl]-3H-quinazolin-4-one;

(S)-3-(2-chloro-phenyl)-6-fluoro-2-[2-(4-methyl-pyrimidine-2-yl)-vinyl]-6-fluoro-3H-quinazolin-4-one;

(S)-3-(2-chloro-phenyl)-6-fluoro-2-{2-[6-(isopropylamino-methyl)-pyridin-2-yl]-ethyl}-3H-quinazolin-4-one;

(S)-6-fluoro-2-[2-(2-methyl-thiazol-4-yl)-vinyl]-3-(2-methyl-phenyl)-3H-quinazolin-4-one;

(S)-3-(2-chloro-phenyl)-6-fluoro-2-[2-(2-methyl-thiazol-4-yl)-vinyl]-3H-quinazolin-4-one;

(S)-2-[2-(2-dimethylaminomethyl-thiazol-4-yl)-vinyl]-6-fluoro-3-(2-fluoro-phenyl)-3H-quinazolin-4-one;

(S)-3-(2-bromo-phenyl)-6-fluoro-2-[2-(2-methyl-thiazol-4-yl)-vinyl]-3H-quinazolin-4-one;

(S)-3-(2-chloro-phenyl)-2-[2-(2-methyl-thiazol-4-yl)-vinyl]-3H-quinazolin-4-one;

(S)-3-(2-chloro-phenyl)-6-fluoro-2-(2-pyridin-2-yl-vinyl)-3H-quinazolin-4-one;

(S)-3-(2-bromo-phenyl)-2-(2-pyridin-2-yl-vinyl)-3H-quinazolin-4-one;

(S)-6-chloro-2-(2-pyridin-2-yl-vinyl)-3-o-tolyl-3H-quinazolin-4-one;

(S)-3-(2-chloro-phenyl)-2-[2-(6-methyl-pyridin-2-yl)-vinyl]-3H-quinazolin-4-one;

(S)-6-chloro-2-[2-(6-methyl-pyridin-2-yl)-vinyl]-3-o-tolyl-3H-quinazolin-4-one;

(S)-3-(2-chloro-phenyl)-6-fluoro-2-(2-pyridin-2-yl-ethyl)-3H-quinazolin-4-one;

(S)-6-{2-[3-(2-chloro-phenyl)-6-fluoro-4oxo-3,4-dihydro-quinazolin-2-yl]-vinyl}-pyridine-2-carbaldehyde;

(S)-3-(2-chloro-phenyl)-6-fluoro-2-[2-(6-methylaminomethyl-pyridin-2-yl)-vinyl]-3H-quinazolin-4-one;

(S)-N-(6-{2-(2-chloro-phenyl-6-fluoro-4-oxo-3,4-dihydro-quinazolin-2-yl]-vinyl}-pyridin-2-ylmethyl)-N-methyl-acetamide;

(S)-6-{2-[3-(2-chloro-phenyl)-6-fluoro-4-oxo-3,4-dihydro-quinazolin-2-yl]-vinyl}-pyridine-2-carbonitrile;

(S)-3-(2-fluoro-phenyl)-2-(2-pyridin-2-yl-vinyl)-3H-quinazolin-4-one;

(S)-3-(2-bromo-phenyl)-6-fluoro-2-(2-pyridin-2-yl-vinyl)-3H-quinazolin-4-one;

(S)-3-(4-bromo-2-chloro-phenyl)-6-fluoro-2-(2-pyridin-2-yl-vinyl)-3H-quinazolin-4-one;

(S)-3-(2-chloro-phenyl)-2-[2-(6-diethylaminomethyl-pyridin-2-yl)-vinyl]-3H-quinazolin-4-one;

(S)-N-(6-{2-[3-(2-chloro-phenyl)-6-fluoro-4-oxo-3,4-dihydro-quinazolin-2-yl]-vinyl}-pyridin-2-ylmethyl)-N-ethyl-acetamide;

(S)-3-(2-chloro-phenyl)-6-fluoro-2-[2-(6-fluoromethyl-pyridin-2-yl)-vinyl]-3H-quinazolin-4-one;

(S)-3-(2-chloro-phenyl)-6-fluoro-2-[2-(6-pyrrolidin-1-ylmethyl-pyridin-2-yl)-ethyl]-3H-quinazolin-4-one;

(S)-3-(2-chloro-phenyl)-2-[2-(6-{(ethyl-(2-hydroxy-ethyl)-amino]-methyl}-pyridin-2-yl)-vinyl]-6-fluoro-3H-quinazolin-4-one;

(S)-3-(2-chloro-phenyl)-6-fluoro-2-{2-[6-(isopropylamino-methyl)-pyridin-2-yl]-vinyl}-3H-quinazolin-4-one;

(S)-3-(2-chloro-phenyl)-6-fluoro-2-{2-[6-(2-methyl-piperidin-1-ylmethyl)-pyridin-2-yl]-vinyl}-3H-quinazolin-4-one;

(S)-3-(2-chloro-phenyl)-2-[2-(6-ethoxymethyl-pyridin-2-yl)-vinyl]-6-fluoro-3H-quinazolin-4-one;

(S)-3-)2-chloro-phenyl)-2-{2-[6-(2,5-dihydro-pyrrol-1-ylmethyl)-pyridin-2-yl]-vinyl}-6-fluoro-3H-quinazolin-4-one;

(S)-3-(2-chloro-phenyl)-6-fluoro-2-{2-[6-(4-methyl-piperidin-1-ylmethyl)-pyridin-2-yl]-vinyl}-3H-quinazolin-4-one;

(S)-6-bromo-2-[2-(6-methyl-pyridin-2-yl)-vinyl]-3-o-tolyl-3H-quinazolin-4-one;

(S)-6-bromo-2-(2-pyridin-2-yl-vinyl)-3-o-tolyl-3H-quinazolin-4-one;

(S)-6-fluoro-3-(2-fluoro-phenyl)-2-(2-pyridin-2-yl-vinyl)-3H-quinazolin-4-one;

(S)-3-(2-chloro-phenyl)-6-methyl-2-(2-pyridin-2-yl-vinyl)-3H-quinazolin-4-one;

(S)-3-(2-chloro-phenyl)-2-[2-(6-dimethylaminomethyl-pyridin-2-yl)-vinyl]-6-fluoro-3H-quinazolin-4-one;

(S)-6-fluoro-3-(2-fluoro-phenyl)-2-[2-(6-methyl-pyridin-2-yl)-vinyl]-3H-quinazolin-4-one;

(S)-3-(2-chloro-phenyl)-2-[2-(6-{(2-dimethylamino-ethyl)-methyl-amino]-methyl}-pyridin-2-yl)-vinyl]-6-fluoro-3H-quinazolin-4-one;

(S)-3-(2-chloro-phenyl)-6-2-[2-(6-hydroxymethyl-pyridin-2-yl)-vinyl]-3H-quinazolin-4-one;

(S)-acetic acid 6-{2-[3-(2-chloro-phenyl)-6-fluoro-4-oxo-3,4-dihydro-quinazolin-2-yl]-vinyl}-pyridin-2-yl methyl ester;

(S)-6-{2-[3-(2-bromo-phenyl)-6-fluoro-4-oxo-3,4-dihydro-quinazolin-2-yl]-vinyl}-pyridine-2-carbaldehyde;

(S)-3-(2-bromo-phenyl)-2-[2-(6-diethylaminomethyl-pyridin-2-yl)-vinyl]-3H-quinazolin-4-one;

(S)-acetic acid 6-{2-[3-(2-bromo-phenyl)-6-fluoro-4-oxo-3,4-dihydro-quin-azolin-2-yl]-vinyl}-pyridin-2-ylmethyl ester;

(S)-diethylamino-acetic acid 6-{2-[3-(2-chloro-phenyl)-6-fluoro-4-oxo-3,4-dihydro-quinazolin-2-yl]-vinyl}-pyridin-2-ylmethyl ester;

(S)-3-(2-chloro-phenyl)-2-[2-(6-difluoromethyl-pyridin-2-yl)-vinyl]-6-fluoro-3H-quinzaolin-4-one;

(S)-3-(2-chloro-phenyl)-2-[2-(6-methoxy-pyridin-2-yl)-vinyl]-3H-quinazolin-4-one;

(S)-2-{2-[3-(2-chloro-phenyl)-6-fluoro-4-oxo-3,4-dihydro-quinazolin-2-yl]-vinyl}-6-methyl-nicotinonitrile;

(S)-2-{2-[3-(2-chloro-phenyl)-6-fluoro-4-oxo-3,4-dihydro-quinazolin-2-yl]-ethyl}-6-methyl-nicotinonitrile;

(S)-3-(2-chloro-phenyl)-6-fluoro-2-(2-pyrimidine-2-yl-ethyl)-3H-quinazolin-4-one;

(S)-3-(2-chloro-phenyl)-2-[2-(4,6-dimethyl-pyrimidine-2-yl)-vinyl]-6-fluoro-3H-quinazolin-4-one;

(S)-2-{2-[3-(2-chloro-phenyl)-6-fluoro-4-oxo-3,4-dihydro-quinazolin-2-yl]-vinyl}-nicotinonitrile;

(S)-3-(2-chloro-phenyl)-6-fluoro-2-(2-{6-[(3-methyl-butylamino)-methyl]-pyridin-2-yl}-ethyl)-3H-quinazolin-4-one;

(S)-2-{2-[3-(2-chloro-phenyl)-6-fluoro-4-oxo-3,4-dihydro-quinazolin-2-yl]-ethyl}-nicotinonitrile;

(S)-2-[2-(6-chloro-4-oxo-3-o-tolyl-3,4-dihydro-quinazolin-2-yl)-vinyl]-benzonitrile;

(S)-2-{2-[3-(2-chloro-phenyl)-6-fluoro-4-oxo-3,4-dihydro-quinazolin-2-yl]-vinyl}-4-methyl-benzonitrile;

(S)-3-(2-bromo-phenyl)-6-fluoro-2-[2-(6-hydroxymethyl-pyridin-2-yl)-vinyl]-3H-quinazolin-4-one; and (S)-3-(2-chloro-phenyl)-6-fluoro-2-[2-(6-pyrrolidin-1-ylmethyl-pyridin-2-yl_-vinyl]-3H-quinazolin-4-one;

(B) (S)-6-fluoro-2-[2-(2-fluoro-phenyl)-vinyl]-3-(2-methyl-pyridin-3-yl)-3H-quinazolin-4-one;

(S)-2-{2-[6-fluoro-3-(2-methyl-pyridin-3-yl)-4-oxo-3,4-dihydro-quinazolin-2-yl]-vinyl}-benzonitrile;

(S)-2-{2-[6-fluoro-3-(2-methylpyridin-3-yl)-4-oxo-3,4-dihydroquinazolin-2-yl]-vinyl}-benzonitrile;

(S)-2-{2-[3-(2-chloro-pyridin-3-yl)-6-fluoro-4-oxo-3,4-dihydroquinazolin-2-yl]-vinyl}-benzonitrile;

(S)-2-{2-[6-fluoro-3-(2-methyl-pyridin-3-yl)-4-oxo-3,4-dihydro-quinazolin-2-yl]-vinyl}-4-methyl-benzonitrile;

(S)-2-{2-[3-(2-methyl-pyridin-3-yl)-4-oxo-3,4-dihydro-quinazolin-2-yl]-vinyl}-benzonitrile;

(S)-6-fluoro-3-(2-methyl-pyridin-3-yl)-2-[2-(thiazol-2-yl)-vinyl]-3H-quinazolin-4-one;

(S)-6-fluoro-3-(2-methyl-pyridin-3-yl)-2-[2-(2-methyl-thiazol-4-yl)-vinyl]-3H-quinazolin-4-one;

(S)-6-fluoro-3-(2-methyl-pyridin-3-yl)-2-[2-(4-methyl-thiazol-2-yl)-vinyl]-3H-quinazolin-4-one;

(S)-2-[2-(5-diethylaminomethyl-2-fluoro-phenyl)-vinyl]-6-fluoro-3-(2-methyl-pyridin-3-yl)-3H-quinazolin-4-one;

(S)-6-fluoro-2-[2-(2-fluoro-5-pyrrolidin-1-ylmethyl-phenyl)-vinyl]-3-(2-methyl-pyridin-3-yl)-3H-quinazolin-4-one;

(S)-3-(2-chloro-pyridin-3yl)-2-[2-(2-fluoro-phenyl)-vinyl]-3H-quinazolin-4-one;

(S)-3-(2-chloro-pyridin-3-yl)-6-fluoro-2-[2-(6-methyl-phenyl-2-yl)-vinyl]-3H-quinazolin-4-one;

(S)-3-(2-chloro-pyridin-3-yl)-6-fluoro-2-[2-(fluoro-phenyl)-vinyl]-3H-quinazolin-4-one;

(S)-6-chloro-2-[2-(2-fluoro-phenyl)-vinyl]-3-(2-methyl-pyridin-3-yl)-3H-quinazolin-4-one;

(S)-6-chloro-2-[2-(2-fluoro-phenyl)-vinyl]-3-(3-methyl-1-oxy-pyridin-4-yl)-3H-quinazolin-4-one;

(S)-3-{2-(3-(2-chloro-pyridin-3-yl)-6-fluoro-4-oxo-3,4-dihydro-quinazolin-2-yl]-vinyl}-benzaldehyde;

(S)-3-{2-[3-(2-chloro-pyridin-3-yl)-4-oxo-3,4-dihydro-quinazolin-2-yl]-vinyl}-benzaldehyde;

(S)-3-(2-chloro-pyridin-3-yl)-6-fluoro-2-[2-(3-hydroxymethyl-phenyl)-vinyl]-3H-quinazolin-4-one;

(S)-3-(2-chloro-pyridin-3-yl)-2-{2-[3(1,4-dioxa-8-aza-spiro[4.5]dec-8-ylmethyl)-phenyl]-vinyl}-6-fluoro-3-3H-quinazolin-4-one;

(S)-3-(2-chloro-pyridin-3-yl)-6-fluoro-2-{2-[3-(4-pyrrolidin-1-yl-piperidin-1-ylmethyl)-phenyl]-vinyl}-3H-quinazolin-4-one;

(S)-2-{2-[3-(2-chloro-pyridin-3-yl-6-fluoro-4-oxo-3,4-dihydro-quinazolin-2-yl]-vinyl}-benzonitrile;

(S)-2-{2-[3-(2-chloro-pyrdini-3-yl)-4-oxo-3,4-dihydro-quinazolin-2-yl]-vinyl}-benzonitrile;

(S)-2-[2-(2-fluoro-phenyl)-vinyl]-3-(2-methyl-pyridin-3-yl)-3H-quinazolin-4-one;

(S)-3-(2-chloro-pyridin-3-yl)-6-fluoro-2-[2-hydroxy-phenyl)-vinyl]-3H-quinazolin-4-one;

(S)-6-fluoro-3-(2-methyl-pyridin-3-yl)-2-[2-(2-methyl-thiazol-4-yl)-ethyl]-3H-quinazolin-4-one;

(S)-6-fluoro-3-(2-chloro-pyridin-3-yl)-2-[2-(2-dimethylamino-methylthiazol-4-yl)-vinyl]-3H-quinazolin-4-one;

(S)-2-[2-(5-Diethylaminomethyl-2-fluoro-phenyl)-vinyl]-6-fluoro-3-(4-methyl-pyridin-3-yl)-3H-quinazolin-4-one;

(S)-4-Diethylaminomethyl-2-{2-[6-fluoro-3-(4-methyl-pyridin-3-yl)-4-oxo-3,4-dihydro-quinazolin-2-yl]-vinyl}-benzonitrile;

(S)-2-[2-(5-Diethylaminomethyl-2-fluoro-phenyl)-vinyl]-6-fluoro-3-(3-methyl-pyrazin-2-yl)-3H-quinazolin-4-one;

(S)-6-fluoro-3-(2-methyl-pyridin-3-yl)-2-[2-(2-dimethylamino-methylthiazol-4-yl)-vinyl]-3H-quinazolin-4-one;

(S)-6-fluoro-3-(2-methyl-pyridin-3-yl)-2-[2-(2-methyl-oxazol-4-yl)-vinyl]-3H-quinazolin-4-one;

(S)-6-fluoro-3-(2-chloro-pyridin-3-yl)-2-[2-(thiazol-2-yl)-vinyl]-3H-quinazolin-4-one;

(S)-6-fluoro-3-(4-methyl-pyridin-3-yl)-2-[2-(4-methyl-thiazol-2-yl)-vinyl]-3H-quinazolin-4-one;

(S)-3-(2-chloro-pyridin-3-yl)-6-fluoro-2-[2-(2-hydroxy-phenyl)-vinyl]-3H-quinazolin-4-one; and (S)-6-fluoro-2-[2-(2-fluoro-5-pyrrolidin-1-ylmethyl-phenyl)-ethyl]-3-(2-methyl-pyridin-3-yl)-3H-quinazolin-4-one;

(C) 3-(2-chloro-phenyl)-6-fluoro-2-(2-pyridin-2-yl-vinyl)-3H-quinazolin-4-one;

3-(2-bromo-phenyl)-2-(2-pyridin-2-yl)-3H-quinazolin-4-one;

6-chloro-2-(2-pyridin-2-yl-vinyl)-3-o-tolyl-3H-quinazolin-4-one;

3-(2-chloro-phenyl)-2-[2-(6-methyl-pyridin-2-yl)-vinyl]-3H-quinazolin-4-one;

6-chloro-2-[2-(6-methyl-pyridin-2-yl)-vinyl]-3-o-tolyl-3H-quinazolin-4-one;

3-(2-chloro-phenyl)-6-fluoro-2-(2-pyridin-2-yl-ethyl)-3H-quinazolin-4-one;

6-{2-[3-(2-chloro-phenyl)-6-fluoro-4-oxo-3,4-dihydro-quinazolin-2-yl]-vinyl}-pyridine-2-carbaldehyde;

3-(2-chloro-phenyl)-6-fluoro-2-[2-(6-methylaminomethyl-pyridin-2-yl)-vinyl]-3H-quinazolin-4-one;

N-(6-{2-[3-(2-chloro-phenyl)-6-fluoro-4-oxo-3,4-dihydro-quinazolin-2-yl]-vinyl}-pyridin-2-ylmethyl)-N-methyl-acetamide;

3-(2-chloro-phenyl)-2-[2-(4-diethylaminomethyl-pyridin-2-yl)-vinyl]-6-fluoro-3H-quinazolin-4-one;

6-{2-[3-(2-chloro-pheny;)-6-fluoro-4-oxo-3,4-dihydro-quinazolin-2-yl]-vinyl}-pyridine-2-carbonitrile;

3-(2-fluoro-phenyl)-2-(2-pyridin-2-yl-vinyl)-3H-quinazolin-4-one;

3-(2-bromo-phenyl)-6-fluoro-2-(2-pyridin-2-yl-vinyl)-3H-quinazolin-4-one;

3-(4-bromo-2-chloro-phenyl)-6-fluoro-2-(2-pyridin-2-yl-vinyl)-3H-quinazolin-4-one;

3-(2-chloro-phenyl)-2-[2-(6-diethylaminomethyl-pyridin-2-yl)-vinyl]-3H-quinazolin-4-one;

N-(6-{2-[3-(2-chloro-phenyl)-6-fluoro-4-oxo-3,4-dihydro-quinazolin-2-yl]-vinyl}-pyridin-2-ylmethyl)-N-ethyl-acetamide;

3-(2-chloro-phenyl)-6-fluoro-2-[2-(6-fluoromethyl-pyridin-2-yl)-vinyl]-3H-quinazolin-4-one;

3-(2-chloro-phenyl)-6-fluoro-2-[2-(6-pyrrolidin-1-ylmethyl-pyridin-2-yl)-ethyl]-3H-quinazolin-4-one;

3-(2-chloro-phenyl)-2-[2-(6-{(ethyl-(2-hydroxy-ethyl)-amino]-methyl}-pyridin-2-yl)-vinyl]-6-fluoro-3H-quinazolin-4-one;

3-(2-chloro-phenyl)-6-fluoro-2-{2-[6-(isopropylamino-methyl)-pyridin-2-yl]-vinyl}-3H-quinazolin-4-one;

3-(2-chloro-phenyl)-6-fluoro-2-{2-[6-(2-methyl-piperidin-1-ylmethyl)-pyridin-2-yl]-vinyl}-3H-quinazolin-4-one;

3-(2-chloro-phenyl)-2-[2-(6-ethylaminomethyl-pyridin-2-yl)-vinyl]-6-fluoro-3H-quinazolin-4-one;

3-(2-chloro-phenyl)-2-[2-(6-ethoxymethyl-pyridin-2-yl)-vinyl]-6-fluoro-3H-quinazolin-4one;

3-(2-chloro-phenyl)-2-{2-[6-(2,5-dihydro-pyrrol-1-ylmethyl)-pyridin-2-yl]-vinyl}-6-fluoro-3H-quinazolin-4-one;

3-(2-chloro-phenyl)-6-fluoro-2-{2-[6-(4-methyl-piperidin-1-ylmethyl)-pyridin-2-yl]-vinyl}-3H-quinazolin-4-one;

6-bromo-2-[2-(6-methyl-puridin-2-yl)-vinyl]-3-o-tolyl-3H-quinazolin-4-one;

6-bromo-2-(2-pyridin-2-yl-vinyl)-3-o-tolyl-3H-quinazolin-4-one;

6-fluoro-3-(2-fluoro-phenyl)-2-(2-pyridin-2-yl-vinyl)-3H-quinazolin-4-one;

1-benzyl-5-(2-methyl-[1,3]dioxolan-2-yl)-2-oxo-2,3-dihydro-1H-indole-3-carboxylic acid (3-phenylcarbamoyl-phenyl)-amide;

3-(2-chloro-phenyl)-6-methyl-2-(2-pyridin-2-yl-vinyl)-3H-quinazolin-4-one;

3-(2-chloro-phenyl)-2-[2-(6-dimethylaminomethyl-pyridin-2-yl)-vinyl]-6-fluoro-3H-quinazolin-4-one;

6-fluoro-3-(2-fluoro-phenyl)-2-[2-(6-methyl-pyridin-2-yl)-vinyl]-3H-quinazolin-4-one;

3-(2-chloro-phenyl)-2-[2-(6-{[(2-dimethylamino-ethyl)-methyl-amino]-methyl}-pyridin-2-yl)-vinyl]-6-fluoro-3H-quinazolin-4-one;

3-(2-chloro-phenyl)-6-fluoro-2-[2-(6-hydroxymethyl-pyridin-2-yl)-vinyl]-3H-quinazolin-4-one;

acetic acid 6-{2-[3-(2-chloro-phenyl)-6-fluoro-4-oxo-3,4-dihydro-quinazolin-2-yl]-vinyl}-pyridin-2-ylmethyl ester;

6-{2-[3-(2-bromo-phenyl)-6-fluoro-4-oxo-3,4-dihydro-quinazolin-2-yl]-vinyl}-pyridine-2-carbaldehyde;

3-(2-bromo-phenyl)-2-[2-(6-diethylaminomethyl-pyridin-2-yl)-vinyl]-6-fluoro-3H-quinazolin-4-one;

3-(2-bromo-phenyl)-2-[2-(6-diethylaminomethyl-pyridin-2-yl)-vinyl]-3H-quinazolin-4-one;

acetic acid 6-{2-[3-(2-bromo-phenyl)-6-fluoro-4-oxo-3,4-dihydro-quinazolin-2-yl]-vinyl}-pyridin-2-ylmethyl ester;

3-(2-chloro-phenyl)-6-fluoro-2-[2-(6-methoxymethyl-pyridin-2-yl)-vinyl]-3H-quinzolin-4-one;

diethylamino-acetic acid 6-{2-[3-(2-chloro-phenyl)-6-fluoro-4-oxo-3,4-dihydro-quinazolin-2-yl]-vinyl}-pyridin-2-ylmethyl ester;

6-fluoro-3-(2-methyl-pyridin-3-yl)-2-[2-(2-methyl-thiazol-4-yl)-vinyl]-3H-quinazolin-4-one;

3-(2-bromo-phenyl)-6-fluoro-2-[2-(6-hydroxymethyl-pyridin-2-yl)vinyl]-3H-quinazolin-4-one; and, 3-(2-chloro-phenyl)-6-fluoro-2-[2-(6-pyrrolidin-1-ylmethyl-pyridin-2-yl)-vinyl]-3H-quinazolin-4-one;

(D) 6-Chloro-3-(2-chloro-phenyl)-2-[2-hydroxy-2-(6-methyl-pyridin-2-yl)-vinyl]-3H-quinazolin-4-one;

2-{2-[3-(2-Chloro-phenyl)-4-oxo-3,4-dihydro-quinazolin-2-yl]-1-hydroxy-vinyl}-nicotinonitrile;

2-{2-[3-(2-Chloro-pyrid-3-yl)-6-fluoro-4-oxo-3,4-dihydro-quinazolin-2-yl]-1-hydroxy-vinyl}-nicotinonitrile;

2-{2-[6-Chloro-3-(2-methyl-phenyl)-4-oxo-3,4-dihydro-quinazolin-2-yl]-1-hydroxy-vinyl}-nicotinonitrile;

3-(2-Chloro-phenyl)-2-[2-(3-diethylaminomethyl-phenyl)-2-hydroxy-ethoxy]-6-fluoro-3H-quinazolin-4-one;

3-(2-Chloro-phenyl)-6-fluoro-2-[2-(3-pyrrolidin-1-ylmethyl-phenyl)-2-hydroxy-ethyl]-3H-quinazolin-4-one;

3-(2-Chloro-pyrid-3-yl)-2-[2-(3-diethylaminomethyl-phenyl)-2-hydroxy-ethyl]-6-fluoro-3H-quinazolin-4-one;

2-[2-(3-Diethylaminomethyl-phenyl)-2-hydroxy-ethyl]-6-fluoro-3-(2-fluoro-phenyl)-3H-quinazolin-4-one;

2-[2-(3-Diethylaminomethyl-phenyl)-2-hydroxy-ethyl]-3-(2-fluoro-phenyl)-3H-quinazolin-4-one;

3-(2-chloro-phenyl)-2-[2-(6-diethylaminomethyl)-pyridin-2-yl)-2-hydroxy-vinyl]-6-fluoro-3H-quinazolin-4-one;

2-{2-[3-(2-Chloro-pyrid-3-yl)-6-fluoro-4-oxo-3,4-dihydro-quinazolin-2-yl]-1-hydroxy-vinyl}-6-methyl-nicotinonitrile;

2-{2-[3-(2-Chloro-phenyl)-4-oxo-3,4-dihydro-quinazolin-2-yl]-1-hydroxy-vinyl)-6-methyl-nicotinonitrile;

2-{2-[6-Chloro-3-(2-chloro-phenyl)-4-oxo-3,4-dihydro-quinazolin-2-yl]-1-hydroxy-vinyl}-6-methyl-nicotinonitrile;

2-{2-[3-(2-Chloro-phenyl)-6-fluoro-4-oxo-3,4-dihydro-quinazolin-2-yl]-1-hydroxy-vinyl}-6-fluoro-nicotinonitrile;

2-{2-[3-(2-Chloro-phenyl)-6-fluoro-4-oxo-3,4-dihydro-quinazolin-2-yl]-1-hydroxy-vinyl}-4-fluoro-benzonitrile;

2-{2-[3-(2-Chloro-phenyl)-6-fluoro-4-oxo-3,4-dihydro-quinazolin-2-yl]-1-hydroxy-vinyl}-4-methyl-benzonitrile;

2-{2-[3-(2-Chloro-phenyl)-4-oxo-3,4-dihydro-thieno[3,2d]pyrimidin-2-yl]-1-hydroxy-vinyl}-6-methyl-nicotinonitrile;

2-{2-[3-(2-methyl-phenyl)-4-oxo-3,4-dihydro-thieno[3,2d]pyrimidin-2-yl]-1-hydroxy-vinyl}-6-methyl-nicotinonitrile;

2-{2-[3-(2-Chloro-pyrid-3yl)-4-3,4-dihydro-thieno[3,2-d]pyrimidin-2-yl]-1-hydroxy-vinyl}-4-methyl-benzonitrile;

2-{2-[3-(2-Chloro-phenyl)-4-oxo-3,4-dihydro-thieno[3,2-d]pyrimidin-2-yl]-1-hydroxy-vinyl}-4-fluoro-benzonitrile;

2-{2-[3-(2-Fluoro-phenyl)-4-oxo-3,4-dihydro-thieno[3,2-d]pyrimidin-2-yl]-1-hydroxy-vinyl}-4-methyl-benzonitrile;

2-{2-[3-(2-Chloro-phenyl)-4-oxo-3,4-dihydro-thieno[3,2-d]pyrimidin-2-yl]-1-hydroxy-vinyl}-benzonitrile; and, 2-{2-[3-(2-Chloro-pyrid-3yl)-4-oxo-3,4-dihydro-thieno[3,2-d]pyrimidin-2-yl]-1-hydroxy-vinyl}-benzonitrile;

3-(2-chloro-phenyl)-6-fluoro-2-[2-hydroxy-2-(2-methyl-thiazol-4-yl)-vinyl]-3H-quinazolin-4-one;

3-(2-chloro-phenyl)-6-fluoro-2-[2-hydroxy-2-(6-methyl-pyridin-2-yl)-vinyl]-3H-quinazolin-4-one;

2-{2-[3-(2-chloro-phenyl)-6-fluoro-4-oxo-3,4-dihydro-quinazolin-2-yl]-1-hydroxy-vinyl}-6-methyl-nicotinonitrile;

2-{2-[3-(2-chloro-phenyl)-6-fluoro-4-oxo-3,4-dihydro-quinazolin-2-yl]-1-hydroxy-vinyl}-nicotinonitrile;

2-{2-[3-(2-chloro-phenyl)-6-fluoro-4-oxo-3,4-dihydro-quinazolin-2-yl]-1-hydroxy-vinyl}-benzonitrile;

2-{2-[3-(2-chloro-pyridin-3-yl)-6-fluoro-4-oxo-3,4-dihydro-quinazolin-2-yl]-1-hydroxy-vinyl}-6-methyl-nicotinonitrile;

3-(2-chloro-phenyl)-6-fluoro-2-(2-hydroxy-2-pyridin-2-yl-vinyl)-3H-quinazolin-4-one;

2-{2-[6-fluoro-3-(2-methyl-pyridin-3-yl)-4-oxo-3,4-dihydro-quinazolin-2-yl]-1-hydroxy-vinyl}-benzonitrile;

2-{2-[3-(2-chloro-pyridin-3-yl)-6-fluoro-4-oxo-3,4-dihydro-quinazolin-2-yl]-1-hydroxy-vinyl}-benzonitrile;

3-(2-chloro-phenyl)-6-fluoro-2-[2-(2-fluoro-phenyl)-2-hydroxy-ethyl]-3H-quinazolin-4-one;

(E) 3-(2-chloro-phenyl)-6-fluoro-2-[(pyridin-2-ylmethyl)-amino]-3H-quinazolin-4-one;

6-fluoro-3-(2-methyl-phenyl)-2-[(pyridin-2-ylmethyl)-amino]-3H-quinazolin-4-one;

3-(2-chloro-phenyl)-6-fluoro-2-[(2-flurophenyl-methyl)-amino]-3H-quinazolin-4-one;

3-(2-chloro-phenyl)-2-[(2-cyanophenyl-methyl)-amino]-6-fluoro-3H-quinazolin-4-one;

3-(2-chloro-phenyl)-2-[(6-diethylaminomethylpyridin-2-ylmethyl)-amino]-6-fluoro-3H-quinazolin-4-one;

3-(2-chloro-phenyl)-6-fluoro-2-[(6-pyrrolidin-1-ylmethyl-pyridin-2-ylmethyl)-amino]-3H-quinazolin-4-one;

3-(2-chloro-phenyl)-2-[(3-pyrrolidin-1-ylmethyl-phenylamino)-methyl]-3H-thieno[3,2-d]pyrimidin-4-one;

3-(2-methyl-phenyl)-2-[(3-pyrrolidin-1-ylmethyl-phenylamino)-methyl]-3H-thieno[3,2-d]pyrimidin-4-one;

3-(2-chloro-phenyl)-2-[(2-fluoro-phenylamino)-methyl]-3H-thieno[3,2d]pyrimidin-4-one;

3-(2-chloro-pyrid-3-yl)-2-[(3-pyrrolidin-1-ylmethyl-phenylamino)-methyl]-3H-thieno[3,2-d]pyrimidin-4-one;

2-{[3-(2-chloro-pyrid-3-yl)-4-oxo-3,4-dihydro-thieno[3,2-d]pyrimidin-2-ylmethyl]-amino}-benzonitrile;

3(2-chloro-phenyl)-2-[(3-pyrrolidin-1-ylmethyl-phenylamino)-methyl]-3H-quinazolin-4-one;

6-chloro-3-(2-chloro-phenyl)-2-[(3-pyrrolidin-1-ylmethyl-phenylamino)-methyl]-3H-quinazolin-4-one;

6-chloro-3-(2-chloro-phenyl)-2-[(3-diethylaminomethyl-phenylamino)-methyl]-3H-quinazolin-4-one;

6-chloro-3-(2-chloro-pyrid-3-yl)-2-[(3-diethylaminomethyl-phenylamino)-methyl]-3H-quinazolin-4-one;

6-chloro-3-(2-trifluoromethyl-phenyl)-2-[(3-diethylaminomethyl-phenylamino)-methyl]-3H-quinazolin-4 -one;

2-{[3-(2-chloro-pyridin-3-yl)-4-oxo-3,4-dihydro-quinazolin-2-ylmethyl]-amino}-benzonitrile;

2-{[3-(2-methyl-pyridin-3-yl)-4-oxo-3,4-dihydro-quinazolin-2-ylmethyl]-amino}-benzonitrile;

2-{[6-fluoro-3-(2-methyl-phenyl)-4-oxo-3,4-dihydro-quinazolin-2-ylmethyl]-amino}-nicotinonitrile;

2-{[3-(2-chloro-phenyl)-4-oxo-3,4-dihydro-quinazolin-2-ylmethyl]-amino}-nicotinonitrile;

2-{[3-(2-chloro-pyridin-3-yl)-6-fluoro-4-oxo-3,4-dihydro-quinazolin-2-ylmethyl]-amino}-benzonitrile;

3-{[3-(2-chloro-phenyl)-6-fluoro-4-oxo-3,4-dihydro-quinazolin-2-ylmethyl]-amino}-benzonitrile;

3-(2-chloro-phenyl)-2-[(3-diethylaminomethyl-phenylamino)-methyl]-6-fluoro-3H-quinazolin-4-one;

3-(2-chloro-phenyl)-6-fluoro-2-(pyrimidin-2-ylaminomethyl)-3H-quinazolin-4-one;

3-(2-chloro-pyridin-3-yl)-6-fluoro-2-(m-tolylamino-methyl)-3H-quinazolin-4-one;

3-(2-chloro-pyridin-3-yl)-6-fluoro-2-[(6-methyl-pyridin-2-ylamino)-methyl]-3H-quinazolin-4-one;

3-(2-chloro-phenyl)-6-fluoro-2-(pyridin-2-ylaminomethyl)-3H-quinazolin-4-one;

3-(2-chloro-pyridin-3-yl)-6-fluoro-2-[(3-pyrrolidin-1-ylmethyl-phenylamino)-methyl]-3H-quinazolin-4-one;

6-fluoro-3-(2-methyl-pyridin-3-yl)-2-[(3-pyrrolidin-1-ylmethyl-phenylamino)-methyl]-3H-quinazolin-4-one;

3-(2-chloro-phenyl)-6-fluoro-2-[(2-fluoro-benzylamino)-methyl]-3H-quinazolin-4-one;

N-(3-{[3-3-(2-chloro-phenyl)-6-fluoro-4-oxo-3,4-dihydro-quinazolin-2-ylmethyl]-amino}-phenyl)-acetamide;

3-(2-chloro-phenyl)-6-fluoro-2-[(3-pyrrolidin-1-ylmethyl-phenylamino)-methyl]-3H-quinazolin-4-one;

2-{[3-(2-chloro-phenyl)-6-fluoro-4-oxo-3,4-dihydro-quinazolin-2-ylmethyl]-amino}-nicotinonitrile;

3-(2-chloro-pyridin-3-yl)-6-fluoro-2-[(2-fluoro-phenylamino)-methyl]-3H-quinazolin-4-one;

3-(2-chloro-phenyl)-6-fluoro-2-[(2-fluoro-phenylamino)-methyl]-3H-quinazolin-4-one;

3-(2-chloro-phenyl)-6-fluoro-2-[(6-methyl-pyridin-2-ylamino)-methyl]-3H-quinazolin-4-one; and, (F) an atropisomer of the formula

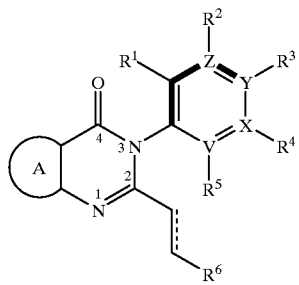

I wherein either V, X, Y and Z are all carbon or one of them is nitrogen and the others are carbon;

each of $R^1$, $R^2$, $R^3$, $R^4$ and $R^5$ is selected, independently, from hydrogen, halogen, $(C_1-C_6)$alkyl, trifluoromethyl, cyano, $(C_1-C_6)$alkosy, $(C_1-C_6)$alkylthio and C(=O)—)—$(C_1-C_6)$alkyl, with the proviso that: (a) $R^1$ can not be the same as $R^5$, when each of V, X, and Z is carbon; (b) at least one of $R^1$ and $R^5$ must be other than hydrogen; and (c) when V, X, Y or Z is nitrogen, then $R^5$, $R^4$, $R^3$ or $R^2$ respectively, is absent;

ring A is a fused heteroaromatic ring, wherein said heteroaromatic ring is a 5 or 6 membered heteroaromatic ring, wherein said 6 membered heteroaromatic ring, taken together with the carbon atoms common to both rings of the bicyclic system, has the formula

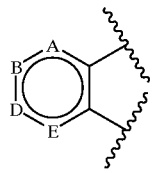

and wherein said 5 membered heteroaromatic ring, taken together with the carbon atoms common to both rings of the bicyclic system, has the formula

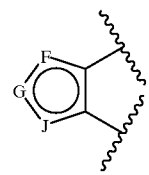

wherein said ring positions "A", "B", "D" and "E" may be independently selected from carbon or nitrogen;
  wherein said ring positions "F", "G" and "J" may be independently selected from carbon, nitrogen, oxygen or sulfur, with the proviso that: (a) if more than two of "F", "G" or "J" is a heteroatom then said 5 membered heteroaromatic ring isselected from the group consisting of (1,2,3)-triazole, (1,2,3)-thiadiazole, (1,2,5)-thiadiazole, and (1,2,5)-oxadiazole; and (b) if two of "F", "G" or "J" are heteroatoms, only one of said heteroatoms may be oxygen or sulfur;
  wherein said fused heteroaromatic rings may optionally be independently substituted on any of the carbon or nitrogen atoms capable of forming an additional bond with a substituent selected from hydrogen, $(C_1-C_6)$ alkyl, halogen, trifluoromethyl, amino—$(CH_2)_n$—, $(C_1-C_6)$alkylamino-$(CH_2)_n$—, di$(C_1-C_6)$alkylamino—$(CH_2)_n$-, $(C_1-C_6)$alkoxy, hydroxy$(C_1-C_6)$ alkyl, $(C_1-C_6)$alkyl—O—$(C_1-C_6)$alkyl—, —CN, $(C_1-C_6)$alkyl—CO—O—$(C_1-C_6)$alkyl-, $(C_1-C_6)$alkyl, $(C_1-C_6)$alkyl—CO—O—, hydroxy, —$NO_2$, $R^{15}$—C (=O)—, $R^{15}$—O—C(=O)—, di$(C_1-C_6)$alkyl—N—C (=O)—, $(C_3-C_7)$cycloalkyl, and $R^{15}$—NH—C (=O)—, and phenyl optionally substituted with halo, $C_1-C_6$)alkyl, —CN, or —$CF_3$;

$R^6$ is phenyl of the formual $Ph^1$ or a five or six membered heterocycle, wherein said 6-membered heterocycle has the formula

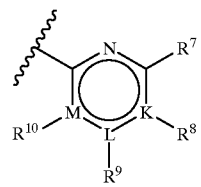

wherein "N" is nitrogen; wherein said ring positions "K", "L" and "M" may be independently selcted from carbon or nitrogen, with the proviso that only one of "K", "L" or "M" can be nitrogen;

wherein said five membered heterocycle has the formual

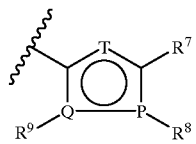

wherein said ring positions "P", "Q" and "T" may be independently selected from carbon, nitrogen, oxygen or sulfur; with the proviso that only one of "P", "Q" "T" can be oxygen or sulfur and at least on of "P", "Q" or "T" must be a heteroatom;

wherein said $Ph^1$ is a group of the formula

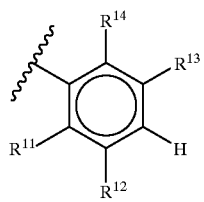

wherein each $R^{15}$ is, independently, hydrogen or $(C_1-C_6)$ alkyl;

each of $R^9$, $R^{10}$ and $R^{11}$ is selected, independently, from hydrogen, $(C_1-C_6)$alkyl optionally substituted with one to three halogen atoms, halo, $CF_3$, $(C_1-C_6)$alkyl optionally one to three halogen atoms, $(C_1-C_6)$alkylthiol, $R^{16}O$—$(CH_2)_p$—, $(C_1-C_6)$alkyl—NH—$(CH_2)_p$—, di$(C_1-C_6)$alkyl—N—$(CH_2)_p$—, $(C_3-C_7)$cycloalkyl—NH—$(CH_2)_p$—, $H_2N$—(C=O)—$(CH_2)_p$—, $(C_1-C_6)$ alkyl—NH—(C=O)— $(CH_2)_p$—, di$(C_1-C_6)$alkyl—N—(C=O)—$(CH_2)_p$—, $(C_3-C_7)$cycloalkyl—NH—(C=O)—$(CH_2)_p$—, $R^{16}O$—(C=O)—$(CH_2)_p$—, $(C_1-C_6)$alkyl—(O=O)—O—$(C_1-C_6)$alkyl—, ($C_1$-$C_6$)alkyl—O—(O=C)—O—($C_1$-$C_6$)-alkyl—,
($C_1$-$C_6$)alkyl—(O=C)—O—, ($C_1$-$C_6$)alkyl—
(O=)—NH—($CH_2$)$_p$—, H(O=C)—NH—($CH_2$)$_p$—,
($C_1$-$C_6$)alkyl—(O=C)—N—[($C_1$-$C_6$)alkyl]($CH_2$)$_p$—, H(O=C)—N—[($C_1$-$C_6$)alkyl]($CH_2$)$_p$—,
hydroxy, H—C(=O)—($CH_2$)$_p$—, ($C_1$-$C_6$)alkyl—C(=O)—, ($C_1$-$C_6$)alkyl—O— C(=O)—, $R^{15}$—($CH_2$)$_p$—O—C(=O)—, amino—($CH_2$)$_p$—, hydroxy—($C_1$-$C_6$)alkyl—, ($C_1$-$C_6$)alkyl—O—($C_1$-$C_6$)alkyl— and cyano;

each of $R^7$, $R^{12}$ and $R^{13}$ is selected, independently, from hydrogen, ($C_1$-$C_6$)alkyl optionally substituted with one to threee halogen atoms, halogen, $CF_3$, ($C_1$-$C_6$)alkoxy optionally substituted with one to three halogen atoms, ($C_1$-$C_6$)alkylthiol, $R^{16}$O—($CH_2$)$_p$—, ($C_1$-$C_6$)alkyl—NH—($CH_2$)$_p$—, di($C_1$-$C_6$)alkyl—N—($CH_2$)$_p$—, ($C_3$-$C_7$)cycloalkyl—NH—($CH_2$)$_p$—, ($C_1$-$C_6$)alkyl—HN—(C=O)— ($CH_2$)$_p$—, di($C_1$-$C_6$)alkyl—N—(C=O)—($CH_2$)$_p$—, ($C_3$-$C_7$)cycloalkyl—NH—(C=O)—$CH_2$)$_p$—, $R^{16}$O—(C=O)—($CH_2$)$_p$—, ($C_1$-$C_6$)alkyl—(O=O)—O—($C_1$-$C_6$)alkyl—, ($C_1$-$C_6$)alkyl—O—(O=C)—O—($C_1$-$C_6$)-alkyl—, ($C_1$-$C_6$)alkyl—(O=C)—O—, ($C_1$-$C_6$)alkyl—(O=)—NH—($CH_2$)$_p$—, H(O=C)—NH—($CH_2$)$_p$—, ($C_1$-$C_6$)alkyl—(O=C)—N—[($C_1$-$C_6$)alkyl]($CH_2$)$_p$—, H(O=C)—N—[($C_1$-$C_6$)alkyl]($CH_2$)$_p$—, hydroxy, H—C(=O)—($CH_2$)$_p$—, ($C_1$-$C_6$)alkyl—C(=O)—, ($C_1$-$C_6$)alkyl—O— C(=O)—, $R^{15}$—($CH_2$)$_p$—O—C(=O)—, amino—($CH_2$)$_p$—, hydroxy—($C_1$-$C_6$)alkyl—, ($C_1$-$C_6$)alkyl—O—($C_1$-$C_6$)alkyl—
—CHO and cyano;

each $R^{14}$ is, independently, hydrogen or halogen;
each $R^{16}$ is, independently, hydrogen, ($C_1$-$C_6$)alkyl, ($C_1$-$C_6$)alkyl—(C=O)—, ($C_1$-$C_6$)alkyl—O—(C=O)—, ($C_1$-$C_6$)alkyl—NH—(C=O)—, or di($C_1$-$C_6$)alkyl—N—(C=O)—;

each is hydrogen, cyano, ($C_1$-$C_6$)alkyl, halogen, trifluoromethyl, —CHO or ($C_1$-$C_6$)alkoxy;

n is an integer from zero to 3;
p is an integer from zero to 3; and
wherein the dashed bond represented an optiona double bond;
with the proviso that when $R^{11}$ is hydrogen, one of $R^{13}$ and $R^{14}$ is other than hydrogen.

2. The method of claim 1 wherein said dopamine agonist therapy is therapy comprising the administration of L-dopa or L-dopa in combination with an inhibitor of peripheral dopadecarboxylase.

3. The method of claim 2 wherein said inhibitor of peripheral dopadecarboxylase is carbidopa or benserazide.

4. The method of claim 2 wherein said compound is a compound of group (A) or a pharmaceutically acceptable salt thereof.

5. The method of claim 2 wherein said compound is a compound of group (B) or a pharmaceutically acceptable salt thereof.

6. A method of treating dyskinesia associated with dopamine agonist therapy in a mammal which comprises administering to said mammal an AMPA receptor antagonizing effective amount of a compound within group (A), (B), (C), (D), (E), or (F), or a pharmaceutically acceptable salt of said compound, wherein groups (A), (B), (C), (D), (E), and (F) are as follows:

(A) (S)-3-(2-chloro-phenyl)-2-[2-(5-diethylaminomethyl-2-fluoro-phenyl)-vinyl]-6-fluoro-3H-quinazolin-4-one;
(S)-3-(2-chloro-phenyl)-2-[2-(6-diethylaminomethyl-pyridin-2-yl)-vinyl]-6-fluoro-3H-quinazolin-4-one;
(S)-3-(2-chloro-phenyl)-2-[2-(4-diethylaminomethyl-pyridin-2-yl)-vinyl]-6-fluoro-3H-quinazolin-4-one;
(S)-3-(2-chloro-phenyl)-2-[2-(6-ethylaminomethyl-pyridin-2-yl)-vinyl]-6-fluoro-3H-quinazolin-4-one;
(S)-3-(2-bromo-phenyl)-2-[2-(6-diethylaminomethyl-pyridin-2-yl)-vinyl]-6-fluoro-3H-quinazolin-4-one;
(S)-3-(2-chloro-phenyl)-6-fluoro-2-[2-(6-methoxymethyl-pyridin-2-yl)-vinyl]-3H-quinazolin-4-one;
(S)-3-(2-chloro-phenyl)-6-fluoro-2-[2-(4-methyl-pyrimidine-2-yl)-vinyl]-3H-quinazolin-4-one;
(S)-3-(2-chloro-phenyl)-6-fluoro-2-{2-[6-isopropylamino-methyl)-pyridin-2-yl]-ethyl}-3H-quinazolin-4-one;
(S)-6-fluoro-2-[2-(2-methyl-thiazol-4-yl)-vinyl]-3-(2-methyl-phenyl)-3H-quinazolin-4-one;
(S)-3-(2-chloro-phenyl)-6-fluoro-2-[2-(2-methyl-thiazol-4-yl)-vinyl]-3H-quinazolin-4-one;
(S)-2-[2-(2-dimethylaminomethyl-thiazol-4-yl)-vinyl]-6-fluoro-3-(2-fluoro-phenyl)-3H-quinazolin-4-one;
(S)-3-(2-bromo-phenyl)-6-fluoro-2-[2-(2-methyl-thiazol-4-yl)-vinyl]-3H-quinazolin-4-one;
(S)-3-(2-chloro-phenyl)-2-[2-(2-methyl-thiazol-4-yl)-vinyl]-3H-quinazolin-4-one;
(S)-3-(2-chloro-phenyl)-6-fluoro-2-(2-pyridin-2-yl-vinyl)-3H-quinazolin-4-one;
(S)-3-(2-bromo-phenyl)-2-(2-pyridin-2-yl-vinyl)-3H-quinazolin-4-one;
(S)-6-chloro-2-(2-pyridin-2-yl-vinyl)-3-o-tolyl-3H-quinazolin-4-one;
(S)-3-(2-chloro-phenyl)-2-[2-(6-methyl-pyridin-2-yl)-vinyl]-3H-quinazolin-4-one;
(S)-6-chloro-2-[2-(6-methyl-pyridin-2-yl)-vinyl]-3-o-tolyl-3H-quinazolin-4-one;
(S)-3-(2-chloro-phenyl)-6-fluoro-2-(2-pyridin-2-yl-ethyl)-3H-quinazolin-4-one;
(S)-6-{2-[3-(2-chloro-phenyl)-6-fluoro-4-oxo-3,4-dihydro-quinazolin-2-yl]-vinyl}-pyridine-2-carbaldehyde;
(S)-3-(2-chloro-phenyl)-6-fluoro-2-[2-(6-methylaminomethyl-pyridin-2-yl)-vinyl]-3H-quinazolin-4-one;
(S)-N-(6-{2-(2-chloro-phenyl-6-fluoro-4-oxo-3,4-dihydro-quinazolin-2-yl]-vinyl}-pyridin-2-ylmethyl)-N-methyl-acetamide;
(S)-6-{2-[3-(2-chloro-phenyl)-6-fluoro-4-oxo-3,4-dihydro-quinazolin-2-yl]-vinyl}-pyridine-2-carbonitrile;
(S)-3-(2-fluoro-phenyl)-2-(2-pyridin-2-yl-vinyl)-3H-quinazolin-4-one;
(S)-3-(2-bromo-phenyl)-6-fluoro-2-(2-pyridin-2-yl-vinyl)-3H-quinazolin-4-one;
(S)-3-(2-chloro-phenyl)-2-[2-(6-diethylaminomethyl-pyridin-2-yl)-vinyl]-3H-quinazolin-4-one;
(S)-N-(6-{2-[3-(2-chloro-phenyl)-6-fluoro-4-oxo-3,4-dihydro-quinazolin-2-yl]-vinyl}-pyridin-2-ylmethyl)-N-ethyl-acetamide;
(S)-3-(2-chloro-phenyl)-6-fluoro-2-[2-(6-fluoromethyl-pyridin-2-yl)-vinyl]-3H-quinazolin-4-one;
(S)-3-(2-chloro-phenyl)-6-fluoro-[2-(6-pyrrolidin-1-ylmethyl-pyridin-2-yl)-ethyl]-3H-quinazolin-
(S)-3-(2-chloro-phenyl)-2-[2-(6-{(ethyl-(2-hydroxy-ethyl)-amino]-methyl}-pyridin-2-yl)-vinyl]-6-fluoro-3H-quinazolin-4-one;

(S)-3-(2-chloro-phenyl)-6-fluoro-2-{2-[6-(isopropylamino-methyl)-pyridin-2-yl]-vinyl}-3H-quinazolin-4-one;

(S)-3-(2-chloro-phenyl)-6-fluoro-2-{2-[6-(2-methyl-piperidin-1-ylmethyl)-pyridin-2-yl]-vinyl-4-one;

(S)-3-(2-chloro-phenyl)-2-[2-(6-ethoxymethyl-pyridin-2-yl)-vinyl]-6-fluoro-3H-quinazolin-4-one;

(S)-3-(2-chloro-phenyl)-2-{2-[6-(2,5-dihydro-pyrrol-1-ylmethyl)-pyridin-2-yl]-vinyl}-6-3H-quinazolin-4-one;

(S)-3-(2-chloro-phenyl)-6-fluoro-2-{2-[6-(4-methyl-piperidin-1-ylmethyl)-pyridin-2-yl]-vin -3H-quinazolin-4-one;

(S)-6-bromo-2-[2-(6-methyl-pyridin-2-yl)-vinyl]-3-o-tolyl-3H-quinazolin-4-one;

(S)-6-bromo-2-(2-pyridin-2-yl-vinyl)-3-o-tolyl-3H-quinazolin-4-one;

(S)-6-fluoro-3-(2-fluoro-phenyl)-2-(2-pyridin-2-yl-vinyl)-3H-quinazolin-4-one;

(S)-3-(2-chloro-phenyl)-6-methyl-2-(2-pyridin-2-yl-vinyl)-3H-quinazolin-4-one;

(S)-3-(2-chloro-phenyl)-2-[2-(6-dimethylaminomethyl-pyridin-2-yl)-vinyl]-6-fluoro-3H-quinazolin-4-one;

(S)-6-fluoro-3-(2-fluoro-phenyl)-2-[2-(6-methyl-pyridin-2-yl)-vinyl]-3H-quinazolin-4-one;

(S)-3-(2-chloro-phenyl)-2-[2-(6-{(2-dimethylamino-ethyl)-methyl-amino]-methyl}-pyridin-2-yl)-vinyl]-6-fluoro-3H-quinazolin-4-one;

(S)-3-(2-chloro-phenyl)-6-2-[2-(6-hydroxymethyl-pyridin-2-yl)-vinyl]-3H-quinazolin-4-one;

(S)-acetic acid 6-{2-[3-(2-chloro-phenyl)-6-fluoro-4-oxo-3,4-dihydro-quinazolin-2-yl]-vinyl}-pyridin-2-yl methyl ester;

(S)-6-{2-[3-(2-bromo-phenyl)-6-fluoro-4-oxo-3,4-dihydro-quinazolin-2-yl]-vinyl}-pyridine-2-carbaldehyde;

(S)-3-(2-bromo-phenyl)-2-[2-(6-diethylaminomethyl-pyridin-2-yl)-vinyl]-3H-quinazolin-4-one;

(S)-acetic acid 6-{2-[3-(2-bromo-phenyl)-6-fluoro-4-oxo-3,4-dihydro-quin-azolin-2-yl]-vinyl}-pyridin-2-ylmethyl ester;

(S)-diethylamino-acetic acid 6-{2-[3-(2-chloro-phenyl)-6-fluoro-4-oxo-3,4-dihydro-quinazolin-2-yl]-vinyl}-pyridin-2-ylmethyl ester;

(S)-3-(2-chloro-phenyl)-2-[2-(6-difluoromethyl-pyridin-2-yl)-vinyl]-6-fluoro-3H-quinzaolin-4-one;

(S)-3-(2-chloro-phenyl)-2-[2-(6-methoxy-pyridin-2-yl)-vinyl]-3H-quinazolin-4-one;

(S)-2-{2-[3-(2-chloro-phenyl)-6-fluoro-4-oxo-3,4-dihydro-quinazolin-2-yl]-vinyl}-6-methyl-nicotinonitrile;

(S)-2-{2-[3-(2-chloro-phenyl)-6-fluoro-4-oxo-3,4-dihydro-quinazolin-2-yl]-ethyl}-6-methyl-nicotinonitrile;

(S)-3-(2-chloro-phenyl)-6-fluoro-2-(2-pyrimidine-2-yl-ethyl)-3H-quinazolin-4-one;

(S)-3-(2-chloro-phenyl)-2-[2-(4,6-dimethyl-pyrimidine-2-yl)-vinyl]-6-fluoro-3H-quinazolin-4-one;

(S)-2-{2-[3-(2-chloro-phenyl)-6-fluoro-4-oxo-3,4-dihydro-quinazolin-2-yl]-vinyl}-nicotinonitrile;

(S)-3-(2-chloro-phenyl)-6-fluoro-2-(2-{6-[(3-methyl-butylamino)-methyl]-pyridin-2-yl}-ethyl)-3H-quinazolin-4-one;

(S)-2-{2-[3-(2-chloro-phenyl)-6-fluoro-4-oxo-3,4-dihydro-quinazolin-2-yl]-ethyl}-nicotinonitrile;

(S)-2-[2-(6-chloro-4-oxo-3-o-tolyl-3,4-dihydro-quinazolin-2-yl)-vinyl]-benzonitrile;

(S)-2-{2-[3-(2-chloro-phenyl)-6-fluoro-4-oxo-3,4-dihydro-quinazolin-2-yl]-vinyl}-4-methyl-benzonitrile;

(S)-3-(2-bromo-phenyl)-6-fluoro-2-[2-(6-hydroxymethyl-pyridin-2-yl)-vinyl]-3H-quinazolin-4-one; and (S)-3-(2-chloro-phenyl)-6-fluoro-2-[2-(6-pyrrolidin-1-ylmethyl-pyridin-2-yl_-vinyl]-3H-quinazolin-4-one;

(B) (S)-6-fluoro-2-[2-(2-fluoro-phenyl)-vinyl]-3-(2-methyl-pyridin-3-yl)-3H-quinazolin-4-one;

(S)-2-{2-[6-fluoro-3-(2-methyl-pyridin-3-yl)-4-oxo-3,4-dihydro-quinazolin-2-yl]-vinyl}-benzonitrile;

(S)-2-{2-[6-fluoro-3-(2-methylpyridin-3-yl)-4-oxo-3,4-dihydroquinazolin-2-yl]-vinyl}-benzonitrile;

(S)-2-{2-[3-(2-chloro-pyridin-3-yl)-6-fluoro-4-oxo-3,4-dihydroquinazolin-2-yl]-vinyl}-benzonitrile;

(S)-2-{2-[6-fluoro-3-(2-methyl-pyridin-3-yl)-4-oxo-3,4-dihydro-quinazolin-2-yl]-vinyl}-4-methyl-benzonitrile;

(S)-2-{2-[3-(2-methyl-pyridin-3-yl)-4-oxo-3,4-dihydro-quinazolin-2-yl]-vinyl}-benzonitrile;

(S)-6-fluoro-3-(2-methyl-pyridin-3-yl)-2-[2-(thiazol-2-yl)-vinyl]-3H-quinazolin-4-one;

(S)-6-fluoro-3-(2-methyl-pyridin-3-yl)-2-[2-(2-methyl-thiazol-4-yl)-vinyl]-3H-quinazolin-4-one;

(S)-6-fluoro-3-(2-methyl-pyridin-3-yl)-2-[2-(4-methyl-thiazol-2-yl)-vinyl]-3H-quinazolin-4-one;

(S)-2-[2-(5-diethylaminomethyl-2-fluoro-phenyl)-vinyl]-6-fluoro-3-(2-methyl-pyridin-3-yl)-3H-quinazolin-4-one;

(S)-6-fluoro-2-[2-(2-fluoro-5-pyrrolidin-1-ylmethyl-phenyl)-vinyl]-3-(2-methyl-pyridin-3-yl)-3H-quinazolin-4-one;

(S)-3-(2-chloro-pyridin-3yl)-2-[2-(2-fluoro-phenyl)-vinyl]-3H-quinazolin-4-one;

(S)-3-(2-chloro-pyridin-3-yl)-6-fluoro-2-[2-(6-methyl-phenyl-2-yl)-vinyl]-3H-quinazolin-4-one;

(S)-3-(2-chloro-pyridin-3-yl)-6-fluoro-2-[2-(fluoro-phenyl)-vinyl]-3H-quinazolin-4-one;

(S)-6-chloro-2-[2-(2-fluoro-phenyl)-vinyl]-3-(2-methyl-pyridin-3-yl)-3H-quinazolin-4-one;

(S)-6-chloro-2-[2-(2-fluoro-phenyl)-vinyl]-3-(3-methyl-1-oxy-pyridin-4-yl)-3H-quinazolin-4-one;

(S)-3-{2-[3-(2-chloro-pyridin-3-yl)-6-fluoro-4-oxo-3,4-dihydro-quinazolin-2-yl]-vinyl}-benzaldehyde;

(S)-3-{2-[3-(2-chloro-pyridin-3-yl)-4-oxo-3,4-dihydro-quinazolin-2-yl]-vinyl}-benzaldehyde;

(S)-3-(2-chloro-pyridin-3-yl)-6-fluoro-2-[2-(3-hydroxymethyl-phenyl)-vinyl]-3H-quinazolin-4-one;

(S)-3-(2-chloro-pyridin-3-yl)-2-{2-[3(1,4-dioxa-8-aza-spiro[4.5]dec-8-ylmethyl)-phenyl]-vinyl}-6-fluoro-3-3H-quinazolin-4-one;

(S)-3-(2-chloro-pyridin-3-yl)-6-fluoro-2-{2-[3-(4-pyrrolidin-1-yl-piperidin-1-ylmethyl)-phenyl]-vinyl}-3H-quinazolin-4-one;

(S)-2-{2-[3-(2-chloro-pyridin-3-yl-6-fluoro-4-oxo-3,4-dihydro-quinazolin-2-yl]-vinyl}-benzonitrile;

(S)-2-{2-[3-(2-chloro-pyrdini-3-yl)-4-oxo-3,4-dihydro-quinazolin-2-yl]-vinyl}-benzonitrile;

(S)-2-[2-(2-fluoro-phenyl)-vinyl]-3-(2-methyl-pyridin-3-yl)-3H-quinazolin-4-one;

(S)-3-(2-chloro-pyridin-3-yl)-6-fluoro-2-[2-hydroxy-phenyl)-vinyl]-3H-quinazolin-4-one;

(S)-6-fluoro-3-(2-methyl-pyridin-3-yl)-2-[2-(2-methyl-thiazol-4-yl)-ethyl]-3H-quinazolin-4-one;

(S)-6-fluoro-3-(2-chloro-pyridin-3-yl)-2-[2-(2-dimethylamino-methylthiazol-4-yl)-vinyl]-3H-quinazolin-4-one;

(S)-2-[2-(5-Diethylaminomethyl-2-fluoro-phenyl)-vinyl]-6-fluoro-3-(4-methyl-pyridin-3-yl)-3H-quinazolin-4-one;

(S)-4-Diethylaminomethyl-2-{2-[6-fluoro-3-(4-methyl-pyridin-3-yl)-4-oxo-3,4-dihydro-quinazolin-2-yl]-vinyl}-benzonitrile;

(S)-2-[2-(5-Diethylaminomethyl-2-fluoro-phenyl)-vinyl]-6-fluoro-3-(3-methyl-pyrazin-2-yl)-3H-quinazolin-4-one;

(S)-6-fluoro-3-(2-methyl-pyridin-3-yl)-2-[2-(2-dimethylamino-methylthiazol-4-yl)-vinyl]-3H-quinazolin-4-one;

(S)-6-fluoro-3-(2-methyl-pyridin-3-yl)-2-[2-(2-methyl-oxazol-4-yl)-vinyl]-3H-quinazolin-4-one;

(S)-6-fluoro-3-(2-chloro-pyridin-3-yl)-2-[2-(thiazol-2-yl)-vinyl]-3H-quinazolin-4-one;

(S)-6-fluoro-3-(4-methyl-pyridin-3-yl)-2-[2-(4-methyl-thiazol-2-yl)-vinyl]-3H-quinazolin-4-one;

(S)-3-(2-chloro-pyridin-3-yl)-6-fluoro-2-[2-(2-hydroxy-phenyl)-vinyl]-3H-quinazolin-4-one; and (S)-6-fluoro-2-[2-(2-fluoro-5-pyrrolidin-1-ylmethyl-phenyl)-ethyl]-3-(2-methyl-pyridin-3-yl)-3H-quinazolin-4-one;

(C) 3-(2-chloro-phenyl)-6-fluoro-2-(2-pyridin-2-yl-vinyl)-3H-quinazolin-4-one;

3-(2-bromo-phenyl)-2-(2-pyridin-2-yl)-3H-quinazolin-4-one;

6-chloro-2-(2-pyridin-2-yl-vinyl)-3-o-tolyl-3H-quinazolin-4-one;

3-(2-chloro-phenyl)-2-[2-(6-methyl-pyridin-2-yl)-vinyl]-3H-quinazolin-4-one;

6-chloro-2-[2-(6-methyl-pyridin-2-yl)-vinyl]-3-o-tolyl-3H-quinazolin-4-one;

3-(2-chloro-phenyl)-6-fluoro-2-(2-pyridin-2-yl-ethyl)-3H-quinazolin-4-one;

6-{2-[3-(2-chloro-phenyl)-6-fluoro-4-oxo-3,4-dihydro-quinazolin-2-yl]-vinyl}-pyridine-2-carbaldehyde;

3-(2-chloro-phenyl)-6-fluoro-2-[2-(6-methylaminomethyl-pyridin-2-yl)-vinyl]-3H-quinazolin-4-one;

N-(6-{2-[3-(2-chloro-phenyl)-6-fluoro-4-oxo-3,4-dihydro-quinazolin-2-yl]-vinyl}-pyridin-2-ylmethyl)-N-methyl-acetamide;

3-(2-chloro-phenyl)-2-[2-(4-diethylaminomethyl-pyridin-2-yl)-vinyl]-6-fluoro-3H-quinazolin-4-one;

6-{2-[3-(2-chloro-pheny;)-6-fluoro-4-oxo-3,4-dihydro-quinazolin-2-yl]-vinyl}-pyridine-2-carbonitrile;

3-(2-fluoro-phenyl)-2-(2-pyridin-2-yl-vinyl)-3H-quinazolin-4-one;

3-(2-bromo-phenyl)-6-fluoro-2-(2-pyridin-2-yl-vinyl)-3H-quinazolin-4-one;

3-(4-bromo-2-chloro-phenyl)-6-fluoro-2-(2-pyridin-2-yl-vinyl)-3H-quinazolin-4-one;

3-(2-chloro-phenyl)-2-[2-(6-diethylaminomethyl-pyridin-2-yl)-vinyl]-3H-quinazolin-4-one;

N-(6-{2-[3-(2-chloro-phenyl)-6-fluoro-4-oxo-3,4-dihydro-quinazolin-2-yl]-vinyl}-pyridin-2-ylmethyl)-N-ethyl-acetamide;

3-(2-chloro-phenyl)-6-fluoro-2-[2-(6-fluoromethyl-pyridin-2-yl)-vinyl]-3H-quinazolin-4-one;

3-(2-chloro-phenyl)-6-fluoro-2-[2-(6-pyrrolidin-1-ylmethyl-pyridin-2-yl)-ethyl]-3H-quinazolin-4-one;

3-(2-chloro-phenyl)-2-[2-(6-{(ethyl-(2-hydroxy-ethyl)-amino]-methyl}-pyridin-2-yl)-vinyl]-6-fluoro-3H-quinazolin-4-one;

3-(2-chloro-phenyl)-6-fluoro-2-{2-[6-(isopropylamino-methyl)-pyridin-2-yl]-vinyl}-3H-quinazolin-4-one;

3-(2-chloro-phenyl)-6-fluoro-2-{2-[6-(2-methyl-piperidin-1-ylmethyl)-pyridin-2-yl]-vinyl}-3H-quinazolin-4-one;

3-(2-chloro-phenyl)-2-[2-(6-ethylaminomethyl-pyridin-2-yl)-vinyl]-6-fluoro-3H-quinazolin-4-one;

3-(2-chloro-phenyl)-2-[2-(6-ethoxymethyl-pyridin-2-yl)-vinyl]-6-fluoro-3H-quinazolin-4one;

3-(2-chloro-phenyl)-2-{2-[6-(2,5-dihydro-pyrrol-1-ylmethyl)-pyridin-2-yl]-vinyl}-6-fluoro-3H-quinazolin-4-one;

3-(2-chloro-phenyl)-6-fluoro-2-{2-[6-(4-methyl-piperidin-1-ylmethyl)-pyridin-2-yl]-vinyl}-3H-quinazolin-4-one;

6-bromo-2-[2-(6-methyl-puridin-2-yl)-vinyl]-3-o-tolyl-3H-quinazolin-4-one;

6-bromo-2-(2-pyridin-2-yl-vinyl)-3-o-tolyl-3H-quinazolin-4-one;

6-fluoro-3-(2-fluoro-phenyl)-2-(2-pyridin-2-yl-vinyl)-3H-quinazolin-4-one;

1-benzyl-5-(2-methyl-[1,3]dioxolan-2-yl)-2-oxo-2,3-dihydro-1H-indole-3-carboxylic acid (3-phenylcarbamoyl-phenyl)-amide;

3-(2-chloro-phenyl)-6-methyl-2-(2-pyridin-2-yl-vinyl)-3H-quinazolin-4-one;

3-(2-chloro-phenyl)-2-[2-(6-dimethylaminomethyl-pyridin-2-yl)-vinyl]-6-fluoro-3H-quinazolin-4-one;

6-fluoro-3-(2-fluoro-phenyl)-2-[2-(6-methyl-pyridin-2-yl)-vinyl]-3H-quinazolin-4-one;

3-(2-chloro-phenyl)-2-[2-(6-{[(2-dimethylamino-ethyl)-methyl-amino]-methyl}-pyridin-2-yl)-vinyl]-6-fluoro-3H-quinazolin-4-one;

3-(2-chloro-phenyl)-6-fluoro-2-[2-(6-hydroxymethyl-pyridin-2-yl)-vinyl]-3H-quinazolin-4-one;

acetic acid 6-{2-[3-(2-chloro-phenyl)-6-fluoro-4-oxo-3,4-dihydro-quinazolin-2-yl]-vinyl}-pyridin-2-ylmethyl ester;

6-{2-[3-(2-bromo-phenyl)-6-fluoro-4-oxo-3,4-dihydro-quinazolin-2-yl]-vinyl}-pyridine-2-carbaldehyde;

3-(2-bromo-phenyl)-2-[2-(6-diethylaminomethyl-pyridin-2-yl)-vinyl]-6-fluoro-3H-quinazolin-4-one;

3-(2-bromo-phenyl)-2-[2-(6-diethylaminomethyl-pyridin-2-yl)-vinyl]-3H-quinazolin-4-one;

acetic acid 6-{2-[3-(2-bromo-phenyl)-6-fluoro-4-oxo-3,4-dihydro-quinazolin-2-yl]-vinyl}-pyridin-2-ylmethyl ester;

3-(2-chloro-phenyl)-6-fluoro-2-[2-(6-methoxymethyl-pyridin-2-yl)-vinyl]-3H-quinzolin-4-one;

diethylamino-acetic acid 6-{2-[3-(2-chloro-phenyl)-6-fluoro-4-oxo-3,4-dihydro-quinazolin-2-yl]-vinyl}-pyridin-2-ylmethyl ester;

6-fluoro-3-(2-methyl-pyridin-3-yl)-2-[2-(2-methyl-thiazol-4-yl)-vinyl]-3H-quinazolin-4-one;

3-(2-bromo-phenyl)-6-fluoro-2-[2-(6-hydroxymethyl-pyridin-2-yl)vinyl]-3H-quinazolin-4-one; and, 3-(2-chloro-phenyl)-6-fluoro-2-[2-(6-pyrrolidin-1-ylmethyl-pyridin-2-yl)-vinyl]-3H-quinazolin-4-one;

(D) 6-Chloro-3-(2-chloro-phenyl)-2-[2-hydroxy-2-(6-methyl-pyridin-2-yl)-vinyl]-3H-quinazolin-4-one;

2-{2-[3-(2-Chloro-phenyl)-4-oxo-3,4-dihydro-quinazolin-2-yl]-1-hydroxy-vinyl}-nicotinonitrile;

2-{2-[3-(2-Chloro-pyrid-3-yl)-6-fluoro-4-oxo-3,4-dihydro-quinazolin-2-yl]-1-hydroxy-vinyl}-nicotinonitrile;

2-{2-[6-Chloro-3-(2-methyl-phenyl)-4-oxo-3,4-dihydro-quinazolin-2-yl]-1-hydroxy-vinyl}-nicotinonitrile;

3-(2-Chloro-phenyl)-2-[2-(3-diethylaminomethyl-phenyl)-2-hydroxy-ethoxy]-6-fluoro-3H-quinazolin-4-one;

3-(2-Chloro-phenyl)-6-fluoro-2-[2-(3-pyrrolidin-1-ylmethyl-phenyl)-2-hydroxy-ethyl]-3H-quinazolin-4-one;

3-(2-Chloro-pyrid-3-yl)-2-[2-(3-diethylaminomethyl-phenyl)-2-hydroxy-ethyl]-6-fluoro-3H-quinazolin-4-one;

2-[2-(3-Diethylaminomethyl-phenyl)-2-hydroxy-ethyl]-6-fluoro-3-(2-fluoro-phenyl)-3H-quinazolin-4-one;

2-[2-(3-Diethylaminomethyl-phenyl)-2-hydroxy-ethyl]-3-(2-fluoro-phenyl)-3H-quinazolin-4-one;

3-(2-chloro-phenyl)-2-[2-(6-diethylaminomethyl)-pyridin-2-yl)-2-hydroxy-vinyl]-6-fluoro-3H-quinazolin-4-one;

2-[2-[3-(2-Chloro-pyrid-3-yl)-6-fluoro-4-oxo-3,4-dihydro-quinazolin-2-yl]-1-hydroxy-vinyl}-6-methyl-nicotinonitrile;

2-{2-[3-(2-Chloro-phenyl)-4-oxo-3,4-dihydro-quinazolin-2-yl]-1-hydroxy-vinyl)-6-methyl-nicotinonitrile;

2-{2-[6-Chloro-3-(2-chloro-phenyl)-4-oxo-3,4-dihydro-quinazolin-2-yl]-1-hydroxy-vinyl}-6-methyl-nicotinonitrile;

2-{2-[3-(2-Chloro-phenyl)-6-fluoro-4-oxo-3,4-dihydro-quinazolin-2-yl]-1-hydroxy-vinyl}-6-fluoro-nicotinonitrile;

2-{2-[3-(2-Chloro-phenyl)-6-fluoro-4-oxo-3,4-dihydro-quinazolin-2-yl]-1-hydroxy-vinyl}-4-fluoro-benzonitrile;

2-{2-[3-(2-Chloro-phenyl)-6-fluoro-4-oxo-3,4-dihydro-quinazolin-2-yl]-1-hydroxy-vinyl}-4-methyl-benzonitrile;

2-{2-[3-(2-Chloro-phenyl)-4-oxo-3,4-dihydro-thieno[3,2d]pyrimidin-2-yl]-1-hydroxy-vinyl}-6-methyl-nicotinonitrile;

2-{2-[3-(2-methyl-phenyl)-4-oxo-3,4-dihydro-thieno[3,2d]pyrimidin-2-yl]-1-hydroxy-vinyl}-6-methyl-nicotinonitrile;

2-{2-[3-(2-Chloro-pyrid-3yl)-4-3,4-dihydro-thieno[3,2-d]pyrimidin-2-yl]-1-hydroxy-vinyl}-4-methyl-benzonitrile;

2-{2-[3-(2-Chloro-phenyl)-4-oxo-3,4-dihydro-thieno[3,2-d]pyrimidin-2-yl]-1-hydroxy-vinyl}-4-fluoro-benzonitrile;

2-{2-[3-(2-Fluoro-phenyl)-4-oxo-3,4-dihydro-thieno[3,2-d]pyrimidin-2-yl]-1-hydroxy-vinyl}-4-methyl-benzonitrile;

2-{2-[3-(2-Chloro-phenyl)-4-oxo-3,4-dihydro-thieno[3,2-d]pyrimidin-2-yl]-1-hydroxy-vinyl}-benzonitrile; and, 2-{2-[3-(2-Chloro-pyrid-3yl)-4-oxo-3,4-dihydro-thieno[3,2-d]pyrimidin-2-yl]-1-hydroxy-vinyl}-benzonitrile;

3-(2-chloro-phenyl)-6-fluoro-2-[2-hydroxy-2-(2-methyl-thiazol-4-yl)-vinyl]-3H-quinazolin-4-one;

3-(2-chloro-phenyl)-6-fluoro-2-[2-hydroxy-2-(6-methyl-pyridin-2-yl)-vinyl]-3H-quinazolin-4-one;

2-{2-[3-(2-chloro-phenyl)-6-fluoro-4-oxo-3,4-dihydro-quinazolin-2-yl]-1-hydroxy-vinyl}-6-methyl-nicotinonitrile;

2-{2-[3-(2-chloro-phenyl)-6-fluoro-4-oxo-3,4-dihydro-quinazolin-2-yl]-1-hydroxy-vinyl}-nicotinonitrile;

2-{2-[3-(2-chloro-phenyl)-6-fluoro-4-oxo-3,4-dihydro-quinazolin-2-yl]-1-hydroxy-vinyl}-benzonitrile;

2-{2-[3-(2-chloro-pyridin-3-yl)-6-fluoro-4-oxo-3,4-dihydro-quinazolin-2-yl]-1-hydroxy-vinyl}-6-methyl-nicotinonitrile;

3-(2-chloro-phenyl)-6-fluoro-2-(2-hydroxy-2-pyridin-2-yl-vinyl)-3H-quinazolin-4-one;

2-{2-[6-fluoro-3-(2-methyl-pyridin-3-yl)-4-oxo-3,4-dihydro-quinazolin-2-yl]-1-hydroxy-vinyl}-benzonitrile;

2-{2-[3-(2-chloro-pyridin-3-yl)-6-fluoro-4-oxo-3,4-dihydro-quinazolin-2-yl]-1-hydroxy-vinyl}-benzonitrile;

3-(2-chloro-phenyl)-6-fluoro-2-[2-(2-fluoro-phenyl)-2-hydroxy-ethyl]-3H-quinazolin-4-one;

(E) 3-(2-chloro-phenyl)-6-fluoro-2-[(pyridin-2-ylmethyl)-amino]-3H-quinazolin-4-one;

6-fluoro-3-(2-methyl-phenyl)-2-[(pyridin-2-ylmethyl)-amino]-3H-quinazolin-4-one;

3-(2-chloro-phenyl)-6-fluoro-2-[(2-flurophenyl-methyl)-amino]-3H-quinazolin-4-one;

3-(2-chloro-phenyl)-2-[(2-cyanophenyl-methyl)-amino]-6-fluoro-3H-quinazolin-4-one;

3-(2-chloro-phenyl)-2-[(6-diethylaminomethylpyridin-2-ylmethyl)-amino]-6-fluoro-3H-quinazolin-4-one;

3-(2-chloro-phenyl)-6-fluoro-2-[(6-pyrrolidin-1-ylmethyl-pyridin-2-ylmethyl)-amino]-3H-quinazolin-4-one;

3-(2-chloro-phenyl)-2-[(3-pyrrolidin-1-ylmethyl-phenylamino)-methyl]-3H-thieno[3,2-d]pyrimidin-4-one;

3-(2-methyl-phenyl)-2-[(3-pyrrolidin-1-ylmethyl-phenylamino)-methyl]-3H-thieno[3,2-d]pyrimidin-4-one;

3-(2-chloro-phenyl)-2-[(2-fluoro-phenylamino)-methyl]-3H-thieno[3,2d]pyrimidin-4-one;

3-(2-chloro-pyrid-3-yl)-2-[(3-pyrrolidin-1-ylmethyl-phenylamino)-methyl]-3H-thieno[3,2-d]pyrimidin-4-one;

2-{[3-(2-chloro-pyrid-3-yl)-4-oxo-3,4-dihydro-thieno[3,2-d]pyrimidin-2-ylmethyl]-amino}-benzonitrile;

3(2-chloro-phenyl)-2-[(3-pyrrolidin-1-ylmethyl-phenylamino)-methyl]-3H-quinazolin-4-one;

6-chloro-3-(2-chloro-phenyl)-2-[(3-pyrrolidin-1-ylmethyl-phenylamino)-methyl]-3H-quinazolin-4-one;

6-chloro-3-(2-chloro-phenyl)-2-[(3-diethylaminomethyl-phenylamino)-methyl]-3H-quinazolin-4-one;

6-chloro-3-(2-chloro-pyrid-3-yl)-2-[(3-diethylaminomethyl-phenylamino)-methyl]-3H-quinazolin-4-one;

6-chloro-3-(2-trifluoromethyl-phenyl)-2-[(3-diethylaminomethyl-phenylamino)-methyl]-3H-quinazolin-4-one;

2-{[3-(2-chloro-pyridin-3-yl)-4-oxo-3,4-dihydro-quinazolin-2-ylmethyl]-amino}-benzonitrile;

2-{[3-(2-methyl-pyridin-3-yl)-4-oxo-3,4-dihydro-quinazolin-2-ylmethyl]-amino}-benzonitrile;

2-{[6-fluoro-3-(2-methyl-phenyl)-4-oxo-3,4-dihydro-quinazolin-2-ylmethyl]-amino}-nicotinonitrile;

2-{[3-(2-chloro-phenyl)-4-oxo-3,4-dihydro-quinazolin-2-ylmethyl]-amino}-nicotinonitrile;

2-{[3-(2-chloro-pyridin-3-yl)-6-fluoro-4-oxo-3,4-dihydro-quinazolin-2-ylmethyl]-amino}-benzonitrile;

3-{[3-(2-chloro-phenyl)-6-fluoro-4-oxo-3,4-dihydro-quinazolin-2-ylmethyl]-amino}-benzonitrile;

3-(2-chloro-phenyl)-2-[(3-diethylaminomethyl-phenylamino)-methyl]-6-fluoro-3H-quinazolin-4-one;

3-(2-chloro-phenyl)-6-fluoro-2-(pyrimidin-2-ylaminomethyl)-3H-quinazolin-4-one;

3-(2-chloro-pyridin-3-yl)-6-fluoro-2-(m-tolylamino-methyl)-3H-quinazolin-4-one;

3-(2-chloro-pyridin-3-yl)-6-fluoro-2-[(6-methyl-pyridin-2-ylamino)-methyl]-3H-quinazolin-4-one;

3-(2-chloro-phenyl)-6-fluoro-2-(pyridin-2-ylaminomethyl)-3H-quinazolin-4-one;

3-(2-chloro-pyridin-3-yl)-6-fluoro-2-[(3-pyrrolidin-1-ylmethyl-phenylamino)-methyl]-3H-quinazolin-4-one;

6-fluoro-3-(2-methyl-pyridin-3-yl)-2-[(3-pyrrolidin-1-ylmethyl-phenylamino)-methyl]-3H-quinazolin-4-one;

3-(2-chloro-phenyl)-6-fluoro-2-[(2-fluoro-benzylamino)-methyl]-3H-quinazolin-4-one;

N-(3-{[3-3-(2-chloro-phenyl)-6-fluoro-4-oxo-3,4-dihydro-quinazolin-2-ylmethyl]-amino}-phenyl)-acetamide;

3-(2-chloro-phenyl)-6-fluoro-2-[(3-pyrrolidin-1-ylmethyl-phenylamino)-methyl]-3H-quinazolin-4-one;

2-{[3-(2-chloro-phenyl)-6-fluoro-4-oxo-3,4-dihydro-quinazolin-2-ylmethyl]-amino}-nicotinonitrile;

3-(2-chloro-pyridin-3-yl)-6-fluoro-2-[(2-fluoro-phenylamino)-methyl]-3H-quinazolin-4-one;

3-(2-chloro-phenyl)-6-fluoro-2-[(2-fluoro-phenylamino)-methyl]-3H-quinazolin-4-one;

3-(2-chloro-phenyl)-6-fluoro-2-[(6-methyl-pyridin-2-ylamino)-methyl]-3H-quinazolin-4-one; and, (F) an atropisomer of the formula

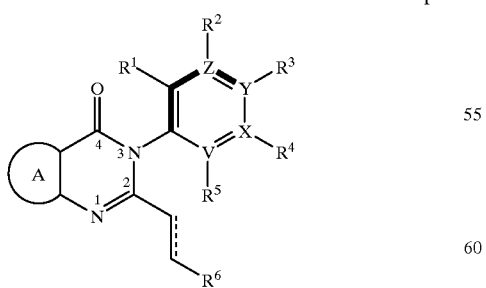

I wherein either V, X, Y and Z are all carbon or one of them is nitrogen and the others are carbon;

each of $R^1$, $R^2$, $R^3$, $R^4$ and $R^5$ is selected, independently, from hydrogen, halogen, $(C_1-C_6)$alkyl, trifluoromethyl, cyano, $(C_1-C_6)$alkosy, $(C_1-C_6)$alkylthio and C(=O)—)—($C_1-C_6$)alkyl, with the proviso that: (a) $R^1$ can not be the same as $R^5$, when each of V, X, and Z is carbon; (b) at least one of $R^1$ and $R^5$ must be other than hydrogen; and (c) when V, X, Y or Z is nitrogen, then $R^5$, $R^4$, $R^3$ or $R^2$ respectively, is absent;

ring A is a fused heteroaromatic ring, wherein said heteroaromatic ring is a 5 or 6 membered heteroaromatic ring, wherein said 6 membered heteroaromatic ring, taken together with the carbon atoms common to both rings of the bicyclic system, has the formula

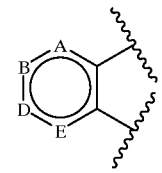

and wherein said 5 membered heteroaromatic ring, taken together with the carbon atoms common to both rings of the bicyclic system, has the formula

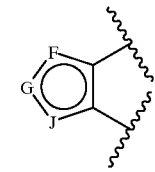

wherein said ring positions "A", "B", "D" and "E" may be independently selected from carbon or nitrogen;

wherein said ring positions "F", "G" and "J" may be independently selected from carbon, nitrogen, oxygen or sulfur, with the proviso that: (a) if more than two of "F", "G" or "J" is a heteroatom then said 5 membered heteroaromatic ring isselected from the group consisting of (1,2,3)-triazole, (1,2,3)-thiadiazole, (1,2,5)-thiadiazole, and (1,2,5)-oxadiazole; and (b) if two of "F", "G" or "J" are heteroatoms, only one of said heteroatoms may be oxygen or sulfur;

wherein said fused heteroaromatic rings may optionally be independently substituted on any of the carbon or nitrogen atoms capable of forming an additional bond with a substituent selected from hydrogen, $(C_1-C_6)$alkyl, halogen, trifluoromethyl, amino—$(CH_2)_n$—, $(C_1-C_6)$alkylamino-$(CH_2)_n$—, di$(C_1-C_6)$alkyl-amino—$(CH_2)_n$-, $(C_1-C_6)$alkoxy, hydroxy$(C_1-C_6)$alkyl, $(C_1-C_6)$alkyl—O—$(C_1-C_6)$alkyl—, —CN, $(C_1-C_6)$alkyl—CO—O—$(C_1-C_6)$alkyl-, $(C_1-C_6)$alkyl, $(C_1-C_6)$alkyl—CO—O—, hydroxy, —$NO_2$, $R^{15}$—C(=O)—, $R^{15}$—O—C(=O)—, di$(C_1-C_6)$alkyl—N—C(=O)—, $(C_3-C_7)$cycloalkyl, and $R^{15}$—NH—C(=O)—, and phenyl optionally substituted with halo, $C_1-C_6$)alkyl, —CN, or —$CF_3$;

$R^6$ is phenyl of the formual $Ph^1$ or a five or six membered heterocycle, wherein said 6-membered heterocycle has the formula

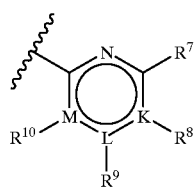

wherein "N" is nitrogen; wherein said ring positions "K", "L" and "M" may be independently selcted from carbon or nitrogen, with the proviso that only one of "K", "L" or "M" can be nitrogen;

wherein said five membered heterocycle has the formual

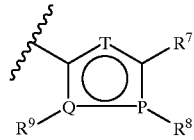

wherein said ring positions "P", "Q" and "T" may be independently selected from carbon, nitrogen, oxygen or sulfur; with the proviso that only one of "P", "Q" "T" can be oxygen or sulfur and at least on of "P", "Q" or "T" must be a heteroatom;

wherein said $Ph^1$ is a group of the formula

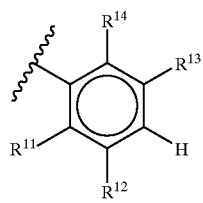

wherein each $R^{15}$ is, independently, hydrogen or $(C_1-C_6)$alkyl;

each of $R^9$, $R^{10}$ and $R^{11}$ is selected, independently, from hydrogen, $(C_1-C_6)$alkyl optionally substituted with one to three halogen atoms, halo, $CF_3$, $(C_1-C_6)$alkyl optionally one to three halogen atoms, $(C_1-C_6)$alkylthiol, $R^{16}O$—$(CH_2)_p$—, $(C_1-C_6)$alkyl—NH—$(CH_2)_p$—, di$(C_1-C_6)$alkyl—N—$(CH_2)_p$—, $(C_3-C_7)$cycloalkyl—NH—$(CH_2)_p$—, $H_2N$—(C=O)—$(CH_2)_p$—, $(C_1-C_6)$alkyl—NH—(C=O)—$(CH_2)_p$—, di$(C_1-C_6)$alkyl—N—(C=O)—$(CH_2)_p$—, $(C_3-C_7)$cycloalkyl—NH—(C=O)—$(CH_2)_p$—, $R^{16}O$—(C=O)—$(CH_2)_p$—, $(C_1-C_6)$alkyl—(O=O)—O—$(C_1-C_6)$alkyl—, $(C_1-C_6)$alkyl—O—(O=C)—O—$(C_1-C_6)$-alkyl—, $(C_1-C_6)$alkyl—(O=C)—O—, $(C_1-C_6)$alkyl—(O=)—NH—$(CH_2)_p$—, H(O=C)—NH—$(CH_2)_p$—, $(C_1-C_6)$alkyl—(O=C)—N—[$(C_1-C_6)$alkyl]$(CH_2)_p$—, H(O=C)—N—[$(C_1-C_6)$alkyl]$(CH_2)_p$—, hydroxy, H—C(=O)—$(CH_2)_p$—, $(C_1-C_6)$alkyl—C(=O)—, $(C_1-C_6)$alkyl—O— C(=O)—, $R^{15}$—$(CH_2)_p$—O—C(=O)—, amino—$(CH_2)_p$—, hydroxy—$(C_1-C_6)$alkyl—, $(C_1-C_6)$alkyl—O—$(C_1-C_6)$alkyl— and cyano;

each of $R^7$, $R^{12}$ and $R^{13}$ is selected, independently, from hydrogen, $(C_1-C_6)$alkyl optionally substituted with one to threee halogen atoms, halogen, $CF_3$, $(C_1-C_6)$alkoxy optionally substituted with one to three halogen atoms, $(C_1-C_6)$alkylthio, $R^{16}O$—$(CH_2)_p$—, $(C_1-C_6)$alkyl—NH—$(CH_2)_p$—, di$(C_1-C_6)$alkyl—N—$(CH_2)_p$—, $(C_3-C_7)$cycloalkyl—NH—$(CH_2)_p$—, $(C_1-C_6)$alkyl—HN—(C=O)— $(CH_2)_p$—, di$(C_1-C_6)$alkyl—N—(C=O)—$(CH_2)_p$—, $(C_3-C_7)$cycloalkyl—NH—(C=O)—$CH_2)_p$—, $R^{16}O$—(C=O)—$(CH_2)_p$—, $(C_1-C_6)$alkyl—(O=O)—O—$(C_1-C_6)$alkyl—, $(C_1-C_6)$alkyl—O—(O=C)—O—$(C_1-C_6)$-alkyl—, $(C_1-C_6)$alkyl—(O=C)—O—, $(C_1-C_6)$alkyl—(O=)—NH—$(CH_2)_p$—, H(O=C)—NH—$(CH_2)_p$—, $(C_1-C_6)$alkyl—(O=C)—N—[$(C_1-C_6)$alkyl]$(CH_2)_p$—, H(O=C)—N—[$(C_1-C_6)$alkyl]$(CH_2)_p$—, hydroxy, H—C(=O)—$(CH_2)_p$—, $(C_1-C_6)$alkyl—C(=O)—, $(C_1-C_6)$alkyl—O— C(=O)—, $R^{15}$—$(CH_2)_p$—O—C(=O)—, amino—$(CH_2)_p$—, hydroxy—$(C_1-C_6)$alkyl—, $(C_1-C_6)$alkyl—O—$(C_1-C_6)$alkyl— —CHO and cyano;

each $R^{14}$ is, independently, hydrogen or halogen;

each $R^{16}$ is, independently, hydrogen, $(C_1-C_6)$alkyl, $(C_1-C_6)$alkyl—(C=O)—, $(C_1-C_6)$alkyl—O—(C=O)—, $(C_1-C_6)$alkyl—NH—(C=O)—, or di$(C_1-C_6)$alkyl—N—(C=O)—;

each is hydrogen, cyano, $(C_1-C_6)$alkyl, halogen, trifluoromethyl, —CHO or $(C_1-C_6)$alkoxy;

n is an integer from zero to 3;

p is an integer from zero to 3; and wherein the dashed bond represented an optiona double bond;

with the proviso that when $R^{11}$ is hydrogen, one of $R^{13}$ and $R^{14}$ is other than hydrogen.

7. The method of claim 6 wherein said dopamine agonist therapy is therapy comprising the administration of L-dopa or L-dopa in combination with an inhibitor of peripheral dopadecarboxylase.

8. The method of claim 7 wherein said inhibitor of peripheral dopadecarboxylase is carbidopa or benserazide.

9. The method of claim 6 wherein said compound is a compound of group (A) or a pharmaceutically acceptable salt thereof.

10. The method of claim 6 wherein said compound is a compound of group (B) or a pharmaceutically acceptable salt thereof.

* * * * *